US007282365B2

(12) United States Patent
Monaci et al.

(10) Patent No.: US 7,282,365 B2
(45) Date of Patent: Oct. 16, 2007

(54) RHESUS HER2/NEU, NUCLEOTIDES ENCODING SAME, AND USES THEREOF

(75) Inventors: Paolo Monaci, Rome (IT); Maurizio Nuzzo, Rome (IT); Nicola La Monica, Rome (IT); Gennaro Ciliberto, Rome (IT); Armin Lahm, Rome (IT)

(73) Assignee: Istituto di Ricerche di Biologia Molecolare P. Angeletti S.p.A., Pomezia (Rome) (IT)

( * ) Notice: Subject to any disclaimer, the term of this patent is extended or adjusted under 35 U.S.C. 154(b) by 0 days.

(21) Appl. No.: 10/541,270

(22) PCT Filed: Dec. 29, 2003

(86) PCT No.: PCT/EP03/14997

§ 371 (c)(1),
(2), (4) Date: Jan. 30, 2006

(87) PCT Pub. No.: WO2004/061105

PCT Pub. Date: Jul. 22, 2004

(65) Prior Publication Data

US 2006/0239969 A1    Oct. 26, 2006

Related U.S. Application Data

(60) Provisional application No. 60/437,846, filed on Jan. 3, 2003.

(51) Int. Cl.
*C07K 14/71* (2006.01)
*C12N 5/10* (2006.01)
*C12N 15/12* (2006.01)
*C07K 14/485* (2006.01)

(52) U.S. Cl. ............ 435/325; 530/350; 536/23.5; 435/69.1; 435/320.1; 435/252.3; 435/254.11

(58) Field of Classification Search ............ None
See application file for complete search history.

(56) References Cited

U.S. PATENT DOCUMENTS

| 5,846,538 A | 12/1998 | Cheever et al. |
| 5,869,445 A | 2/1999 | Cheever et al. |
| 6,127,344 A | 10/2000 | Amici et al. |

FOREIGN PATENT DOCUMENTS

| WO | WO 02/13847 | 2/2002 |
| WO | WO 02/14503 | 2/2002 |
| WO | WO 02/22080 A3 | 3/2002 |

OTHER PUBLICATIONS

Bargmann, et al., "The neu oncogene encodes an epidermal growth factor receptor-related protein", Nature vol. 319, Jan. 16, 1986, pp. 226-230.

Chartier, et al., "Efficient Generation of Recombinant Adenovirus Vectors by Homologous Recombination in *Escherichia coli*", J. of Virology, vol. 70, No. 7, Jul. 1996, pp. 4805-4810.
Cheever, et al., "Immunity to Oncogenic Proteins", Immunological Reviews, No. 145, 1995, pp. 33-59.
Coussens, et al., "Tyrosine Kinase Receptor with Extensive Homology to EGF Receptor Shares Chromosomal Location with neu Oncogene", Science, vol. 230, Dec. 6, 1985, pp. 1132-1139.
Disis, et al., "Oncogenic proteins as tumor antigens", Current Opinion in Immunology, vol. 8, 1996, pp. 637-642.
Disis, et al., "HER-2/neu Protein: A Target for Antigen-Specific Immunotherapy of Human Cancer", Anvances in Cancer Research, vol. 71, pp. 343-371, 1997.
Disis, et al., "Generation of T-Cell Immunity to the HER-2/neu Protein After Active Immunization With HER-2/neu Peptide-Based Vaccines", J. of Clin. Oncol., vol. 20, No. 11, pp. 2624-2632, 2002.
Disis, et al., "Cancer Vaccines Targeting the Her2/neu Oncogenic Protein", Seminars in Oncology, vol. 28, No. 6, Suppl.18, pp. 12-20, Dec. 2001.
Foy, et al., "Vaccination with HER-2 neu DNA or protein subunits protects against growth of a HER-2/neu-expressing murine tumor", Vaccine, vol. 19, pp. 2598-2606, 2001.
King, et al., "Amplification of a Novel v-erbB-Related Gene in a Human Mammary Carcinoma", Science, vol. 229, pp. 974-976, 1985.
Lohrisch, et al., "An Overview of HER2", Seminars in Oncology, vol. 28, No. 6, Suppl 19, Dec. 2001, pp. 3-11.
Montgomery, et al., "Heterologous and Homologous Protection Against Influenza A by DNA Vaccination:Optimization of DNA Vectors", DNA and Cell Biology, vol. 13, No. 9, 777-792, 1993.
Press, et al., "Expression of the HER-2/neu proto-oncogene in normal human adult and fetal tissues", Oncogene, vol. 5, pp. 953-962, 1990.
Shih, et al., "Transforming genes of carcinomas and neuroblastomas introduced into mouse fibroblasts", Nature, vol. 290, Mar. 19, 1981, pp. 261-264.
Shiver, et al., "Cytotoxic T Lymphocyte and Helper T Cell Responses following HIV Polynucleotide Vaccination", Annals New York Academy of Sciences, vol. 772, pp. 198-208, 1996.
Slamon, et al., "Studies of the HER-2/neu Proto-oncogene in Human Breast and Ovarian Cancer", Science, vol. 244, pp. 707-712, May 12, 1989.

(Continued)

*Primary Examiner*—Lorraine Spector
*Assistant Examiner*—Claire M. Kaufman
(74) *Attorney, Agent, or Firm*—Alysia A. Finnegan; Sheldon O. Heber

(57) ABSTRACT

Polynucleotides encoding rhesus monkey HER2/neu have been isolated, cloned and sequenced. The gene encoding the HER2/neu is commonly associated with the development of epithelial-derived human carcinomas. The present invention provides compositions and methods to elicit or enhance immunity to the protein product expressed by the HER2/neu tumor-associated antigen, wherein aberrant HER2/neu expression is associated with a carcinoma or its development. This invention specifically provides adenoviral vector constructs carrying rhHER2/neu and discloses their use in vaccines and pharmaceutical compositions for preventing and treating cancer.

7 Claims, 9 Drawing Sheets

OTHER PUBLICATIONS

Slichenmyer, et al., "Anticancer Therapy Targeting the ErbB Family of Receptor Tyrosine Kinases", Seminars in Oncology, vol. 28, No. 5, Suppl. 16, Oct. 2001, pp. 67-79.

Yarden, Y. "Biology of HER2 and Its Important in Breast Cancer", Oncology, vol. 61 (Suppl 2), 2001, pp. 1-13.

Fendly, et al., "Successful Immunization of Rhesus Monkeys with the Extracellular Domain of p185*HER2*: A Potential Approach to Human Breast Cancer", Vaccine Research, vol. 2, No. 3, pp. 129-139, 1993.

Hung, et al., "*HER-2/neu*-targeting gene therapy—a review", Gene, vol. 159, No. 2, pp. 65-71, 1991.

Nucleotide Sequence of First Rhesus HER2/Neu

```
   1 ATGGAGCTGG CGGCCTGGTA CCGCTGGGGG CTCCTCCTCG CCCTCTTGCC CCCCGGAGCT
  61 GCGGGCACCC AAGTGTGCAC CGGCACAGAC ATGAAGCTGC GGCTCCCTGC CAGTCCCGAG
 121 ACCCACCTGG ACATGCTCCG CCACCTCTAC CAGGGCTGCC AGGTGGTGCA GGGTAACCTG
 181 GAACTCACCT ACCTGCCCAC CAATGCCAGC CTCTCCTTCC TGCAGGATAT CCAGGAGGTG
 241 CAGGGCTACG TGCTCATCGC TCACAACCAA GTGAGGCAGG TCCCACTGCA GAGGCTGCGG
 301 ATTGTGCGAG GCACCCAGCT CTTTGAGGAC AACTATGCCC TGGCCGTGCT AGACAATGGA
 361 GACCTGCTGA ACAATACCAC CCCTGTCACA GGGGCCTCCC CAGGAGGCCT GCGGGAGCTG
 421 CAGCTTCGAA GCCTCACAGA GATCTTGAAA GGAGGGGTCT TGATCCAGCG GAACCCCCAG
 481 CTCTGCTACC AGGACACGAT TTTGTGGAAG GACATCTTCC ATAAGAACAA CCAGCTGGCT
 541 CTCACACTGA TCGACACCAA CCGCTCTCGG GCCTGCCACC CTGTTCTCC AGTGTGTAAG
 601 GGCTCCCGCT GCTGGGGAGA GAGTTCTGAG GATTGTCAGA GCCTGACGCG CACTGTCTGT
 661 GCCGGTGGCT GTGCCCGCTG CAAGGGGCCA CTGCCCACTG ACTGCTGCCA TGAGCAGTGT
 721 GCTGCCGGCT GCACGGGCCC CAAGCACTCT GACTGCCTGG CCTGCCTCCA CTTCAACCAC
 781 AGCGGCATCT GTGARCTGCA CTGCCCAGCC CTGGTCACCT ACAACACAGA CACCTTTGAG
 841 TCCATGCCCA ACCCCGAGGG CCGGTATACA TTCGGCGCCA GCTGTGTGAC TGCCTGTCCC
 901 TACAACTACC TTTCTACGGA CGTGGGATCC TGCACCCTCG TCTGCCCCCT GCACAACCAA
 961 GAGGTGACAG CGGAGGACGG AACACAGCGA TGTGAGAAGT GCAGCAAGCC CTGTGCCCGA
1021 GTGTGCTATG GTCTGGGCAT GGAGCACTTG CGAGAGGTGA GGGCGGTCAC CAGTGCCAAT
1081 ATCCAGGAGT TTGCTGGCTG CAAGAAGATC TTTGGGAGCT TGGCATTTCT GCCAGAGAGC
1141 TTTGATGGCG ACCCAGCCTC CAACACCGCC CCGCTTCAGC CGGAGCAGCT CCGAGTGTTT
1201 GAGACTCTGG AAGAGATCAC AGGTTACCTA TACATCTCAG CATGGCCAGA CAGCCTGCCT
1261 GACCTTAGCG TCCTCCAGAA CCTGCAAGTA ATCCGGGGAC GAATTCTGCA CAATGGCGCC
1321 TACTCACTGA CCCTGCAAGG GCTGGGCATC AGCTGGCTGG GCTGCGCTC GCTGAGGGAA
1381 CTGGGCAGTG GACTGGCCCT CATCCACCAT AACACCCGCC TCTGCTTTGT GCACACGGTG
1441 CCCTGGGACC AGCTCTTCCG GAACCCGCAC CAAGCCCTGC TCCACACTGC AACCGGCCA
1501 GAGGACGAGT GTGTGGGCGA GGGCCTGGCC TGCCACCAGC TGTGCGCCCG AGGGCACTGC
1561 TGGGGTCCAG GCCCACCCA GTGTGTCAAC TGCAGCCAGT TCCTTCGGGG CCAGGAGTGC
1621 GTGGAGGAAT GCCGAGTACT GCAGGGGCTC CCCAGGGAGT ATGTGAATGC AGACACTGT
1681 TTGCCGTGCC ACCCTGAGTG TCAGCCCCAG AATGGCTCAG TGACATGTTT TGGACCGGAG
1741 GCTGACCAGT GTGTGGCCTG TGCCCACTAT AAGGACCCTC CCTTCTGCGT GGCCCGCTGC
1801 CCCAGCGGTG TGAAACCTGA CCTCTCCTAC ATGCCCATCT GGAAGTTTCC AGATGAGGAG
1861 GGCACGTGCC AGTCTTGCCC CATCAACTGC ACCCACTCCT GTGTGGACCT GGATGACAAG
1921 GGCTGCCCCG CCGAGCAGAG AGCCAGCCCT CTGACGTCCA TCATCTCTGC TGTGGTGGGC
1981 ATTCTGCTGG TCGTGGTCTT GGGGGTGGTC TTTGGAATCC TCATCAAGCG ACGGCAGCAG
2041 AAGATCCGGA AGTACACGAT GCGGAGGCTG CTGCAGGAAA CGGAGCTGGT GGAGCCACTG
2101 ACACCGAGTG GAGCGATGCC CAACCAGGCG CAGATGCGGA TCCTGAAAGA GACGGAGCTG
2161 AGGAAGGTGA AGGTGCTTGG ATCTGGAGCT TTTGGCACAG TCTACAAGGG CATCTGGATC
2221 CCTGATGGGG AGAATGTGAA AATTCCAGTG GCCATCAAAG TGTTGAGGGA AAACACATCC
```

FIG.1A

```
2281 CCCAAAGCCA ACAAAGAAAT CTTAGACGAA GCATATGTGA TGGCTGGTGT GGGCTCCCCA
2341 TATGTCTCCC GCCTCCTGGG CATCTGCCTG ACATCCACGG TGCAGCTGGT GACACAGCTT
2401 ATGCCCTATG GCTGCCTCTT AGACCATGTC CGAGAAAACC GCGGACGCCT GGGCTCCCAG
2461 GACCTGCTGA ACTGGTGTAT GCAGATTGCC AAGGGGATGA GCTACCTGGA GGATGTGCGG
2521 CTCGTACACA GGGACTTGGC TGCTCGGAAC GTGCTGGTCA AGAGTCCCAA CCATGTCAAA
2581 ATTACAGACT TTGGGCTGGC TCGGCTGCTG ACATTGACG AGACAGAGTA CCATGCAGAT
2641 GGGGGCAAGG TGCCCATCAA GTGGATGGCG CTGGAGTCCA TTCTCCGACG GCGGTTCACC
2701 CACCAGAGTG ATGTGTGGAG TTATGGTGTG ACTGTGTGGG AGCTGATGAC TTTTGGGGCC
2761 AAACCTTACG ATGGGATCCC AGCCCGGGAG ATCCCTGACC TGCTGGAAAA GGGGGAGCGG
2821 CTGCCCCAGC CCCCCATCTG CACCATTGAT GTCTACATGA TCATGGTCAA ATGTTGGATG
2881 ATTGACTCTG AATGTCGGCC GAGATTCCGG GAGTTGGTGT CGGAATTCTC CCGCATGGCC
2941 AGGGACCCCC AGCGCTTTGT GGTCATCCAG AATGAGGACT TGGGCCCAGC CAGTCCCTTG
3001 GACAGCACCT TCTACCGCTC ACTGCTGGAG GACGATGACA TGGGGGACCT GGTGGATGCT
3061 GAGGAGTATC TGGTACCCCA GCAGGGCTTC TTCTGTCCAG ACCCTGCCCC GGGCACTGGG
3121 GGCATGGTCC ACCACAGGCA CCGCAGCTCA TCTACCAGGA GTGGCGGTGG GGACCTGACG
3181 CTAGGGCTGG AGCCCTCTGA AGAGGAGGCC CCCAGGTCTC CACGGGCACC CTCCGAAGGG
3241 ACTGGCTCTG ATGTATTTGA TGGTGACCTA GGAATGGGGG CAGCCAAGGG GCTGCAAAGC
3301 CTCCCCGCAC ATGACCCCAG CCCTCTACAG CGGTACAGTG AGGACCCCAC GGTACCCCTG
3361 CCTTCTGAGA CTGACGGCTA CGTTGCCCCC CTGACCTGCA GTCCCCAGCC CGAATATGTG
3421 AACCAGCCAG ATGTTCGGCC ACAGCCCCCT TCGCCCCAAG AGGGCCCTCT GTCTCCTGCC
3481 CGACCTACTG GTGCCACTCT GGAAAGGCCC AAGACTCTCT CCCCAGGGAA GAATGGGGTT
3541 GTCAAAGACG TTTTTGCCTT TGGGGGTGCT GTGGAGAACC CCGAGTACTT GGCACCCCGG
3601 GGAGGAGCTG CCCCTCAGCC CCACCTTCCT CCTGCCTTCA GCCCAGCCTT CGACAACCTC
3661 TATTACTGGG ACCAGGACCC ATCAGAGCGG GGGGCTCCAC CTAGCACCTT CAAAGGGACA
3721 CCTACGGCAG AGAACCCAGA GTACCTGGGT CTGGACGTGC CAGTGTGA (SEQ ID NO:1)
```

FIG.1B

Predicted Amino Acid Sequence of First Rhesus
Her2/Neu Protein (SEQ ID NO:2)

```
   1 MELAAWYRWG LLLALLPPGA AGTQVCTGTD MKLRLPASPE THLDMLRHLY QGCQVVQGNL
  61 ELTYLPTNAS LSFLQDIQEV QGYVLIAHNQ VRQVPLQRLR IVRGTQLFED NYALAVLDNG
 121 DLLNNTTPVT GASPGGLREL QLRSLTEILK GGVLIQRNPQ LCYQDTILWK DIFHKNNQLA
 181 LTLIDTNRSR ACHPCSPVCK GSRCWGESSE DCQSLTRTVC AGGCARCKGP LPTDCCHEQC
 241 AAGCTGPKHS DCLACLHFNH SGICELHCPA LVTYNTDTFE SMPNPEGRYT FGASCVTACP
 301 YNYLSTDVGS CTLVCPLHNQ EVTAEDGTQR CEKCSKPCAR VCYGLGMEHL REVRAVTSAN
 361 IQEFAGCKKI FGSLAFLPES FDGDPASNTA PLQPEQLRVF ETLEEITGYL YISAWPDSLP
 421 DLSVLQNLQV IRGRILHNGA YSLTLQGLGI SWLGLRSLRE LGSGLALIHH NTRLCFVHTV
 481 PWDQLFRNPH QALLHTANRP EDECVGEGLA CHQLCARGHC WGPGPTQCVN CSQFLRGQEC
 541 VEECRVLQGL PREYVNARHC LPCHPECQPQ NGSVTCFGPE ADQCVACAHY KDPPFCVARC
 601 PSGVKPDLSY MPIWKFPDEE GTCQSCPINC THSCVDLDDK GCPAEQRASP LTSIISAVVG
 661 ILLVVVLGVV FGILIKRRQQ KIRKYTMRRL LQETELVEPL TPSGAMPNQA QMRILKETEL
 721 RKVKVLGSGA FGTVYKGIWI PDGENVKIPV AIKVLRENTS PKANKEILDE AYVMAGVGSP
 781 YVSRLLGICL TSTVQLVTQL MPYGCLLDHV RENRGRLGSQ DLLNWCMQIA KGMSYLEDVR
 841 LVHRDLAARN VLVKSPNHVK ITDFGLARLL DIDETEYHAD GGKVPIKWMA LESILRRRFT
 901 HQSDVWSYGV TVWELMTFGA KPYDGIPARE IPDLLEKGER LPQPPICTID VYMIMVKCWM
 961 IDSECRPRFR ELVSEFSRMA RDPQRFVVIQ NEDLGPASPL DSTFYRSLLE DDDMGDLVDA
1021 EEYLVPQQGF FCPDPAPGTG GMVHHRHRSS STRSGGGDLT LGLEPSEEEA PRSPRAPSEG
1081 TGSDVFDGDL GMGAAKGLQS LPAHDPSPLQ RYSEDPTVPL PSETDGYVAP LTCSPQPEYV
1141 NQPDVRPQPP SPQEGPLSPA RPTGATLERP KTLSPGKNGV VKDVFAFGGA VENPEYLAPR
1201 GGAAPQPHLP PAFSPAFDNL YYWDQDPSER GAPPSTFKGT PTAENPEYLG LDVPV*
```

FIG.2

Oligonucleotide Primers Spanning Rhesus Her2/neu Gene

| Forward | Sequence | Reverse | Sequence |
|---|---|---|---|
| (-30)-(-10) | AGCCATGGGCGGGCCAGCGCCCA (SEQ ID NO:3) | 96-79 | CTTCATGCTCTGTGCCGCT (SEQ ID NO:20) |
| (-22)-(-1) | GGCCCGGAGCCGAGTGAGCACC (SEQ ID NO:21) | 431-409 | CTTCGAAGCTGCAGCTCCCGCAG (SEQ ID NO:22) |
| 1-25 | ATGGAGCTGGCGGCCTTGTGCCGCT (SEQ ID NO:23) | 812-787 | AGGGCTGGGAGTGCAGTCACAGAT (SEQ ID NO:4) |
| 79-96 | ACCCGCACAGACAATGAAG (SEQ ID NO:24) | 1115-1096 | CCAAAGATCTTCTTTGCAGCC (SEQ ID NO:6) |
| 409-431 | CTTGCCGGCAGCTGCACCTTCGAAG (SEQ ID NO:5) | 1370-1352 | GACCCCAGCCCCAGCCAGC (SEQ ID NO:8) |
| 787-812 | ATCTGTGACTGCACTGCCCAGCCCT (SEQ ID NO:7) | 1583-1558 | CACTGGCTGGGGCCCTGGACCCCAGCA (SEQ ID NO:25) |
| 1096-1115 | GGCTGCAAGCAAGATCTTTGG (SEQ ID NO:9) | 1895-1876 | TGGGTGCAGTTGATGGGGCA (SEQ ID NO:10) |
| 1352-1370 | GCTGGCTGGGGCTGCCCTC (SEQ ID NO:27) | 2183-2161 | GATCCAAGCACCTTCACCTTCCT (SEQ ID NO:26) |
| 1558-1583 | TGCCTGGGGTCCAGGGCCCACCCAGTG (SEQ ID NO:12) | 2222-2200 | GGGATGCAGAGATCGGGCTTGTAGAC (SEQ ID NO:28) |
| 1876-1895 | TGCCCCATCAACTGCACCCA (SEQ ID NO:29) | 2277-K753A-2239 | TCTGTTTTCCCTCAACACGACGATGGCCAGTCGAATTTT (SEQ ID NO:15) |
| 2161-2183 | AGGAAGGTGAAGGTGCTTGGATC (SEQ ID NO:31) | 2378-2356 | GTGGATGTCAGGCAGATCCCAG (SEQ ID NO:30) |
| 2200-2222 | GTCTACAAGCCCGATCTGCATCCC (SEQ ID NO:33) | 2768-2743 | TAAGCTTTGGCCCCAAAAGTCATCAG (SEQ ID NO:32) |
| 2239-K753A 2277 | AAAATTCGACTGGCCATCGTCGTGTTGAGGAAAACACA (SEQ ID NO:16) | 2798-2776 | TCAGGGATCCCGGGCTCAGGGG (SEQ ID NO:13) |
| 2356-2378 | CTGGGCATCTGCCTGACATCCAC (SEQ ID NO:17) | 3410-3388 | GGCTGGGGCTGCAGGTCAGGG (SEQ ID NO:34) |
| 2743-2768 | CTGATGACTTTGGGGCCAAACCTTA (SEQ ID NO:35) | SalI_3768-3746 | GCCGTCGACTTACATGGCAGTCGAGACCCA (SEQ ID NO:19) |
| 2776-2798 | ATCCCAGCCGGGAGAATCCCTGA (SEQ ID NO:37) | 3791-3770 | TTCTGGGGACTGGCCTTCTGG (SEQ ID NO:36) |
| 3388-3410[2] | CCCTGACCTGCAGCCCCAGCC (SEQ ID NO:39) | 3885-3869 | TGGCAGGTTCCCGTGGA (SEQ ID NO:38) |
| 1621-1644 | GTGAGGAAATCCCAGTACTTGCAG (SEQ ID NO:14) | 4166-4145 | GGTTTCAGGGACAGTCTCGAA (SEQ ID NO:18) |
| PmeI_SwaI_RBS_1-16 | CCAGTTTAAACATTTAAATGCCGCCACCATGGAAGCTGGCGGCCT (SEQ ID NO:11) | | |

FIG.3

RT-PCR Primers and Clones Used to Construct Full-Length rhHER2/neu Clone.

| Rxn. # | Oligonucleotide Primer | | Clone |
|---|---|---|---|
| | Forward | Reverse | |
| 1 | AGCCATGGGGCCGGAGCCGCA (SEQ ID NO:3) | AGGGCTGGGCAGTGCAGCTCACAGAT (SEQ ID NO:4) | #1_BS_(-30)-812.A1 |
| 2 | CTGCGGGAGCTGCAGCTTCGAAG (SEQ ID NO:5) | CCAAAGATCTCTTGCAGCC (SEQ ID NO:6) | #1_CR_409_1115.2 |
| 3 | ATCTGTGAGCTGCACTGCCCAGCCT (SEQ ID NO:7) | GAGCGCAGCCCCAGCCAGC (SEQ ID NO:8) | #1_CR_787_1370.10 |
| 4 | GGCTGCAAGAAGATCTTTGG (SEQ ID NO:9) | TGGGTGCAGTTGATGGGGCA (SEQ ID NO:10) | #1_BS_1096_1895.11 |
| 5 | CCAGTTTAAACATTTAAAATGCCGGCACCATGGAGCTGG CGGCCT (SEQ ID NO:11) | TGGGTGCAGTTGATGGGGCA (SEQ ID NO:10) | #1_CR_1-1895.7(-) |
| 6 | TGCTGGGGTCCAGGGCCCCACCCAGTG (SEQ ID NO:12) | TCAGGGATCTCCCGGGCTGGGAT (SEQ ID NO:13) | Not Cloned (1558-2798) |
| 7 | GTGGAGGAATGCCGAGTACTGCAG (SEQ ID NO:14) | TGTGTTTCCCTCAACACGGGCATGGCCACTGGAATTTT (SEQ ID NO:15) | #1_CR_1621-2277.2 |
| 8 | AAAATTCCAGTGGCCATGCCCGTGTTGAGGGAAAACAC A (SEQ ID NO:16) | TCAGGGATCTCCCGGGCTGGGAT (SEQ ID NO:13) | #1_CR_2239-2798.4 |
| 9 | CTGGGCATCTGCCTGACATCCAC (SEQ ID NO:17) | GGTTTCAGGGACAGTCTCTGAA (SEQ ID NO:18) | #1_CR_2356-4166.2 |
| 10 | GTGGAGGAATGCCGAGTACTGCAG (SEQ ID NO:14) | GCCGTCGACTTTACATGGACAGTCCAGACCCA (SEQ ID NO:19) | #1_CR_1621-3768.8(+) |
| 10 | GTGGAGGAATGCCGAGTACTGCAG (SEQ ID NO:14) | GCCGTCGACTTTACATGGACAGTCCAGACCCA (SEQ ID NO:19) | #1_CR_1621-3768.12(+) |

FIG. 4

Nucleotide Sequence of Second Rhesus HER2/Neu

```
   1 ATGGAGCTGG CGGCCTGGTA CCGCTGGGGG CTCCTCCTCG CCCTCTTGCC CCCCGGAGCT
  61 GCGGGCACCC AAGTGTGCAC CGGCACAGAC ATGAAGCTGC GGCTCCCTGC CAGTCCCGAG
 121 ACCCACCTGG ACATGCTCCG CCACCTCTAC CAGGGCTGCC AGGTGGTGCA GGGTAACCTG
 181 GAACTCACCT ACCTGCCCAC CAATGCCAGC CTCTCCTTCC TGCAGGATAT CCAGGAGGTG
 241 CAGGGCTACG TGCTCATCGC TCACAACCAA GTGAGGCAGG TCCCACTGCA GAGGCTGCGG
 301 ATTGTGCGAG GCACCCAGCT CTTTGAGGAC AACTATGCCC TGGCCGTGCT AGACAATGGA
 361 GACCCGCTGA ACAATACCAC CCCTGTCACA GGGGCCTCCC CAGGAGGCCT GCGGGAGCTG
 421 CAGCTTCGAA GCCTCACAGA GATCTTGAAA GGAGGGGTCT TGATCCAGCG GAACCCCCAG
 481 CTCTGCTACC AGGACACGAT TTTGTGGAAG GACATCTTCC ATAAGAACAA CCAGCTGGCT
 541 CTCACACTGA TCGACACCAA CCGCTCTCGG GCCTGCCACC CCTGTTCTCC AGTGTGTAAG
 601 GGCTCCCGCT GCTGGGGAGA GAGTTCTGAG GATTGTCAGA GCCTGACGCG CACTGTCTGT
 661 GCCGGTGGCT GTGCCCGCTG CAAGGGGCCA CTGCCCACTG ACTGCTGCCA TGAGCAGTGT
 721 GCTGCCGGCT GCACGGGCCC CAAGCACTCT GACTGCCTGG CCTGCCTCCA CTTCAACCAC
 781 AGCGGCATCT GTGARCTGCA CTGCCCAGCC CTGGTCACCT ACAACACAGA CACCTTTGAG
 841 TCCATGCCCA ACCCCGAGGG CCGGTATACA TTCGGCGCCA GCTGTGTGAC TGCCTGTCCC
 901 TACAACTACC TTTCTACGGA CGTGGGATCC TGCACCCTCG TCTGCCCCCT GCACAACCAA
 961 GAGGTGACAG CGGAGGACGG AACACAGCGA TGTGAGAAGT GCAGCAAGCC CTGTGCCCGA
1021 GTGTGCTATG GTCTGGGCAT GGAGCACTTG CGAGAGGTGA GGGCGGTCAC CAGTGCCAAT
1081 ATCCAGGAGT TTGCTGGCTG CAAGAAGATC TTTGGGAGYT TGGCATTTCT GCCAGAGAGC
1141 TTTGATGGCG ACCCAGCCTC CAACACCGCC CCGCTTCAGC CGGAGCAGCT CCGAGTGTTT
1201 GAGACTCTGG AAGAGATCAC AGGTTACCTA TACATCTCAG CATGGCCAGA CAGCCTGCCT
1261 GACCTTAGCG TCCTCCAGAA CCTGCAAGTA ATCCGGGGAC GAATTCTGCA CAATGGCGCC
1321 TACTCACTGA CCCTGCAAGG GCTGGGCATC AGCTGGCTGG GCTGCGCTC GCTGAGGGAA
1381 CTGGGCAGTG GACTGGCCCT CATCCACCAT AACACCCGCC TCTGCTTTGT GCACACGGTG
1441 CCCTGGGACC AGCTCTTCCG GAACCCGCAC CAAGCCCTGC TCCACACTGC CAACCGGCCA
1501 GAGGACGAGT GTGTGGGCGA GGGCCTGGCC TGCCACCAGC TGTGCGCCCR AGGGCACTGC
1561 TGGGGTCCAG GGCCCACCCA GTGTGTCAAC TGCAGCCAGT TCCTTCGGGG CCAGGAGTGC
1621 GTGGAGGAAT GCCGAGTACT GCAGGGGCTC CCCAGGGAGT ATGTGAATGC CAGACACTGT
1681 TTGCCGTGCC ACCCTGAGTG TCAGCCCCAG AATGGCTCAG TGACATGTTT TGGACCGGAG
1741 GCTGACCAGT GTGTGGCCTG TGCCCACTAT AAGGACCCTC CCTTCTGCGT GGCCCGCTGC
1801 CCCAGCGGTG TGAAACCTGA CCTCTCCTAC ATGCCCATCT GGAAGTTTCC AGATGAGGAG
1861 GGCACGTGCC AGCCTTGCCC CATCAACTGC ACCCACTCCT GTGTGGACCT GGATGACAAG
1921 GGCTGCCCCG CCGAGCAGAR AGCCAGCCCT CTGACGTCCA TCATCTCTGC TGTGGTGGGC
1981 ATTCTGCTGG TCGTGGTCTT GGGGGTGGTC TTTGGAATCC TCATCAAGCG ACGGCAGCAG
2041 AAGATCCGGA AGTACACGAT GCGGAGGCTG CTGCAGGAAA CGGAGCTGGT GGAGCCACTG
2101 ACACCGAGTG GAGCGATGCC CAACCAGGCG CAGATGCGGA TCCTGAAAGA GACGGAGCTG
2161 AGGAAGGTGA AGGTGCTTGG ATCTGGAGCT TTTGGCACAG TCTACAAGGG CATCTGGATC
2221 CCTGATGGGG AGAATGTGAA AATTCCAGTG GCCATCAAAG TGTTGAGGGA AAACACATCC
```

FIG.5A

```
2281 CCCAAAGCCA ACAAAGAAAT CTTAGACGAA GCATATGTGA TGGCTGGTGT GGGCTCCCCA
2341 TATGTCTCCC GCCTCCTGGG CATCTGCCTG ACATCCACGG TGCAGCTGGT GACACAGCTT
2401 ATGCCCTATG GCTGCCTCTT AGACCATGTC CGAGAAAACC GCGGACGCCT GGGCTCCCAG
2461 GACCTGCTGA ACTGGTGTAT GCAGATTGCC AAGGGGATGA GCTACCTGGA GGATGTGCGG
2522 CTCGTACACA GGGACTTGGC TGCTCGGAAC GTGCTGGTCA AGAGTCCCAA CCATGTCAAA
2581 ATTACAGACT TTGGGCTGGC TCGGCTGCTG GACATTGACG AGACAGAGTA CCATGCAGAT
2641 GGGGGCAAGG TGCCCATCAA GTGGATGGCG CTGGAGTCCA TTCTCCGACG GCGGTTCACC
2701 CACCAGAGTG ATGTGTGGAG TTATGGTGTG ACTGTGTGGG AGCTGATGAC TTTTGGGGCC
2761 AAAACCTTACG ATGGGATCCC AGCCCGGGAG ATCCCTGACC TGCTGGAAAA GGGGGAGCGG
2821 CTGCCCCAGC CCCCCATCTG CACCATTGAT GTCTACATGA TCATGGTCAA ATGTTGGATG
2881 ATTGACTCTG AATGTCGGCC GAGATTCCGG GAGTTGGTGT CGGAATTCTC CCGCATGGCC
2941 AGGGACCCCC AGCGCTTTGT GGTCATCCAG AATGAGGACT TGGGCCCAGC CAGTCCCTTG
3001 GACAGCACCT TCTACCGCTC ACTGCTGGAG GACGATGACA TGGGGGACCT GGTGGATGCT
3061 GAGGAGTATC TGGTACCCCA GCAGGGCTTC TTCTGTCCAG ACCCTGCCCC GGGCACTGGG
3121 GGCATGGTCC ACCACAGGCA CCGCAGCTCA TCTACCAGGA GTGGCGGTGG GGACCTGACG
3181 CTAGGGCTGG AGCCCTCTGA AGAGGAGGCC CCCAGGTCTC CACRGGCACC CTCCGAAGGG
3241 ACTGGCTCTG ATGTATTTGA TGGTGACCTA GGAATGGGGG CAGCCAAGGG GCTGCAAAGC
3301 CTCCCCGCAC ATGACCCCAG CCCTCTACAG CGGTACAGTG AGGACCCCAC GGTACCCCTG
3361 CCTTCTGAGA CTGACGGCTA CGTTGCCCCC CTGACCTGCA GYCCCCAGCC CGAATATGTG
3421 AACCAGCCAG ATGTTCGGCC ACAGCCCCCT TCGCCCCAAG AGGGCCCTCT GTCTCCTGCC
3481 CGACCTACTG GTGCCACTCT GGAAAGGCCC AAGACTCTCT CCCCAGGGAA GAATGGGGTT
3541 GTCAAAGACG TTTTTGCCTT TGGGGGTGCT GTGGAGAACC CCGAGTACTT GGCACCCCGG
3601 GGAGGAGCTG CCCCTCAGCC CCACCTTCCT CCTGCCTTCA GCCCAGCCTT CGACAACCTC
3661 TATTACTGGG ACCAGGACCC ATCAGAGCGG GGGGCTCCAC CTAGCACCTT CAAAGGGACA
3721 CCTACGGCAG AGAACCCAGA GTACCTGGGT CTGGACGTGC CAGTGTGA (SEQ ID NO:40)
```

FIG.5B

Predicted Amino Acid Sequence of Second Rhesus Her2/Neu Protein

```
   1 MELAAWYRWG LLLALLPPGA AGTQVCTGTD MKLRLPASPE THLDMLRHLY QGCQVVQGNL
  61 ELTYLPTNAS LSFLQDIQEV QGYVLIAHNQ VRQVPLQRLR IVRGTQLFED NYALAVLDNG
 121 DPLNNTTPVT GASPGGLREL QLRSLTEILK GGVLIQRNPQ LCYQDTILWK DIFHKNNQLA
 181 LTLIDTNRSR ACHPCSPVCK GSRCWGESSE DCQSLTRTVC AGGCARCKGP LPTDCCHEQC
 241 AAGCTGPKHS DCLACLHFNH SGICELHCPA LVTYNTDTFE SMPNPEGRYT FGASCVTACP
 301 YNYLSTDVGS CTLVCPLHNQ EVTAEDGTQR CEKCSKPCAR VCYGLGMEHL REVRAVTSAN
 361 IQEFAGCKKI FGSLAFLPES FDGDPASNTA PLQPEQLRVF ETLEEITGYL YISAWPDSLP
 421 DLSVLQNLQV IRGRILHNGA YSLTLQGLGI SWLGLRSLRE LGSGLALIHH NTRLCFVHTV
 481 PWDQLFRNPH QALLHTANRP EDECVGEGLA CHQLCAXGHC WGPGPTQCVN CSQFLRGQEC
 541 VEECRVLQGL PREYVNARHC LPCHPECQPQ NGSVTCFGPE ADQCVACAHY KDPPFCVARC
 601 PSGVKPDLSY MPIWKFPDEE GTCQPCPINC THSCVDLDDK GCPAEQXASP LTSIISAVVG
 661 ILLVVVLGVV FGILIKRRQQ KIRKYTMRRL LQETELVEPL TPSGAMPNQA QMRILKETEL
 721 RKVKVLGSGA FGTVYKGIWI PDGENVKIPV AIKVLRENTS PKANKEILDE AYVMAGVGSP
 781 YVSRLLGICL TSTVQLVTQL MPYGCLLDHV RENRGRLGSQ DLLNWCMQIA KGMSYLEDVR
 841 LVHRDLAARN VLVKSPNHVK ITDFGLARLL DIDETEYHAD GGKVPIKWMA LESILRRRFT
 901 HQSDVWSYGV TVWELMTFGA KPYDGIPARE IPDLLEKGER LPQPPICTID VYMIMVKCWM
 961 IDSECRPRFR ELVSEFSRMA RDPQRFVVIQ NEDLGPASPL DSTFYRSLLE DDDMGDLVDA
1021 EEYLVPQQGF FCPDPAPGTG GMVHHRHRSS STRSGGGDLT LGLEPSEEEA PRSPXAPSEG
1081 TGSDVFDGDL GMGAAKGLQS LPAHDPSPLQ RYSEDPTVPL PSETDGYVAP LTCSPQPEYV
1141 NQPDVRPQPP SPQEGPLSPA RPTGATLERP KTLSPGKNGV VKDVFAFGGA VENPEYLAPR
1201 GGAAPQPHLP PAFSPAFDNL YYWDQDPSER GAPPSTFKGT PTAENPEYLG LDVPV*
(SEQ ID NO:41)
```

FIG.6

MUTATIONS IN RHESUS HER2/neu NUCLEOTIDE SEQUENCE

| POSITION | RhHER2#1 | | POSITION | RhHER2#2 | |
|---|---|---|---|---|---|
| 365 | 2 CLONES | C T G / L | 365 | 2 CLONES | C C G / P |
| 795 | 3 CLONES | G A G / E | 795 | 1 CLONE | G A G / E |
|  | 2 CLONES | G A A / E |  | 2 CLONES | G A A / E |
| 1119 | 2 CLONES | A G C / S | 1119 | 3 CLONES | A G T / S |
|  |  |  |  | 2 CLONES | A G C / S |
| 1550 | 3 CLONES | C G A / R | 1550 | 2 CLONES | C A A / Q |
|  |  |  |  | 3 CLONES | C G A / R |
| 1873 | 6 CLONES | T C T / S | 1873 | 11 CLONES | C C T / P |
| 1940 | 2 CLONES | A G A / R | 1940 | 3 CLONES | A A A / K |
|  |  |  |  | 3 CLONES | A G A / R |
| 3224 | 4 CLONES | C G G / R | 3224 | 5 CLONES | C G G / R |
|  |  |  |  | 3 CLONES | C A G / Q |
| 3402 | 2 CLONES | A G T / S | 3402 | 2 CLONES | A G C / S |
|  |  |  |  | 6 CLONES | A G T / S |

FIG.7

RHESUS HER2/NEU, NUCLEOTIDES ENCODING SAME, AND USES THEREOF

CROSS-REFERENCE TO RELATED APPLICATIONS

This application is a 371 of PCT/EP03/14997, international filing date of Dec. 29, 2003, which claims priority to U.S. Ser. No. 60/437,846, filed Jan. 3, 2003, which is hereby incorporated by reference.

FIELD OF THE INVENTION

The present invention relates generally to the detection and therapy of cancer. More specifically, the present invention relates to the rhesus monkey homologue of the tumor associated polypeptide HER2/neu, to isolated nucleic acid molecules which encode this protein, and to recombinant vectors and hosts comprising DNA encoding this protein. This invention also relates to adenoviral vector constructs carrying rhesus HER2/neu and to their use in vaccines and pharmaceutical compositions for preventing and treating cancer.

BACKGROUND OF THE INVENTION

Cancer typically involves the deregulation of genes that contribute to maintaining the cell cycle or controlling cell proliferation, such as growth factors and their receptors, oncogenes and tumor suppressor genes. The products of many of these genes are expressed on the surface of a wide variety of tumor cells and, hence, were designated tumor-associated antigens (TAA). Recent evidence supports the existence of tumor-associated antigens that are capable of eliciting an immune response, making these molecules a target for vaccine therapy. Because many of these gene products are also expressed in normal cells, albeit at lower levels, many cancer vaccines targeting tumor-associated antigens have proven ineffective due to immunotolerance.

The product of the HER2/neu proto-oncogene (also called c-erbB-2) is a transmembrane TAA that is a member of the epidermal growth factor receptor family. The HER2/neu gene was originally cloned from a rat neuroglioblastoma (Shih et al., Nature 290: 261-264 (1981)) and later isolated and characterized from human cells (Coussens et al., Science 230: 1132-39 (1985); King et al., Science 229: 974-76 (1985)). To date, no simian homologs of HER2/neu are available.

HER2/neu has been further classified as a member of the HER family of receptor tyrosine kinases, which consists of four receptors that participate in cell growth and differentiation. The HER receptors contribute to maintaining normal cell growth by binding growth factor ligands as dimers, thereby initiating intracellular signaling cascades which ultimately result in the activation of genes important in cell growth. Although several ligands have been identified for other members of the HER family, a high affinity ligand for the HER2/neu receptor has yet to be found (Lohrisch and Piccart, Semin. Oncol. 28(6): Suppl. 18: 3-11 (2001)).

Low levels of expression of the HER2/neu transcript and the encoded 185 kD protein were detected in normal adult epithelial cells of various tissues, including the skin and breast, and tissues of the gastrointestinal, reproductive and urinary tracts (Press et al., Oncogene 5: 953-962 (1990)). Higher levels of HER2/neu expression were also detected in the corresponding fetal tissues during embryonic development (Press et al., supra).

HER2/neu is commonly overexpressed or amplified in various malignancies such as carcinomas of the breast, ovary, uterus, colon, and prostate, and adenocarcinomas of the lung (reviewed in Disis and Cheever, Adv. Cancer Research 71: 343-371 (1997)). Such overexpression of HER2/neu correlates with a poor prognosis and a higher relapse rate for cancer patients (Slamon et al., Science 244: 707-712 (1989)).

Many cancer patients suffering from malignancies associated with HER2/neu overexpression have had immune responses against the protein product of the HER2/neu oncogene, thus making HER2/neu an immunological target for the development of cancer therapeutics. An effective vaccine exploiting this immune response to HER2/neu must both enhance this immunity to a level that is protective and/or preventive and overcome self-tolerance.

HER2/neu has been proposed as a target for the development of immunological treatments of different malignancies. Different anti-HER2 monoclonal antibodies have been investigated as therapies for breast cancer, with each antibody demonstrating various levels of success (for discussion, see Yarden, Oncology 61(suppl 2): 1-13 (2001)). Amici et al. (U.S. Pat. No. 6,127,344) disclose a method for inducing immunity against HER2/neu by administering an expression vector comprising the full-length human HER2/neu cDNA functionally linked to the human cytomegalovirus promoter. Cheever and Disis disclose methods for immunizing humans against HER2/neu-associated cancers with HER2 peptides (U.S. Pat. No. 5,846,538). Additionally, HER2/neu peptide-based vaccines have been studied in rodent models (for review, see Disis and Cheever, Advances in Cancer Research 71:343-71 (1997)).

Despite the identification of the HER2/neu clones mentioned above, it would be highly desirable to identify additional mammalian genes encoding HER2/neu to allow for the development of a cancer vaccine which is efficacious and not hindered by self-tolerance.

SUMMARY OF THE INVENTION

The present invention relates to isolated or purified nucleic acid molecules polynucleotides) comprising a sequence of nucleotides that encode a novel rhesus monkey HER2/neu protein (also called c-erbB-2, hereinafter designated rhHER2/neu) as set forth in SEQ ID NO:2 and SEQ ID NO:41. The DNA molecules disclosed herein may be transfected into a host cell of choice wherein the recombinant host cell provides a source for substantial levels of an expressed functional rhHER2/neu protein (SEQ ID NO:2 or SEQ ID NO:41).

The present invention further relates to an isolated nucleic acid molecule which encodes mRNA that expresses a novel rhesus monkey HER2/neu protein; this DNA molecule comprising the nucleotide sequence disclosed herein as SEQ ID NO:1. A preferred aspect of this portion of the present invention is disclosed in FIG. 1, which shows a DNA molecule (SEQ ID NO:1) that encodes a novel rhHER2/neu protein (SEQ ID NO:2).

The present invention also provides an isolated nucleic acid molecule which encodes mRNA that expresses a novel rhesus monkey HER2/neu protein; this DNA molecule comprising the nucleotide sequence disclosed herein as SEQ ID NO:40. A preferred aspect of this portion of the present invention is disclosed in FIG. 5, which shows a DNA molecule (SEQ ID NO:40) that encodes a novel rhHER2/neu protein (SEQ ID NO:41).

The present invention also relates to recombinant vectors and recombinant host cells, both prokaryotic and eukaryotic, which contain the nucleic acid molecules disclosed throughout this specification.

The present invention further relates to a process for expressing a rhesus monkey HER2/neu protein in a recombinant host cell, comprising: (a) introducing a vector comprising the nucleic acid as set forth in SEQ ID NO:1 or SEQ ID NO:40 into a suitable host cell; and, (b) culturing the host cell under conditions which allow expression of said rhesus monkey HER2/neu protein.

A preferred aspect of the present invention is a substantially purified form of a rhesus monkey HER2/neu protein which consists of the amino acid sequence disclosed in FIG. 2 (SEQ ID NO:2).

A preferred aspect of the present invention is a substantially purified form of a rhesus monkey HER2/neu protein which consists of the amino acid sequence disclosed in FIG. 6 (SEQ ID NO:41).

Yet another preferred aspect of the present invention relates to a substantially purified, fully processed (including proteolytic processing, glycosylation and/or phosphorylation), mature rhHER2/neu protein obtained from a recombinant host cell containing a DNA expression vector comprising nucleotide sequence as set forth in SEQ ID NO:1 or SEQ ID NO:40, which express the rhHER2/neu protein. It is especially preferred that the recombinant host cell be a eukaryotic host cell, such as a mammalian cell line.

Another aspect of this invention is a method of preventing or treating cancer comprising administering to a mammal a vaccine vector comprising an isolated nucleic acid molecule, the isolated nucleic acid molecule comprising a sequence of nucleotides that encodes a rhesus monkey HER2/neu protein as set forth in SEQ ID NO:2 or SEQ ID NO:41.

The present invention further relates to an adenovirus vaccine vector comprising an adenoviral genome with a deletion in the E1 and E3 regions, and an insert in the E1 region, wherein the insert comprises an expression cassette comprising: (a) a polynucleotide encoding a rhesus monkey HER2/neu protein; and (b) a promoter operably linked to the polynucleotide.

The present invention also relates to a vaccine plasmid comprising a plasmid portion and an expression cassette portion, the expression cassette portion comprising: (a) a polynucleotide encoding a rhesus monkey HER2/neu protein; and (b) a promoter operably linked to the polynucleotide.

Another aspect of the present invention is a method of protecting or a mammal from cancer or treating a mammal suffering from cancer comprising: (a) introducing into the mammal a first vector comprising: i) a polynucleotide encoding a rhesus monkey HER2/neu protein; and ii) a promoter operably linked to the polynucleotide; (b) allowing a predetermined amount of time to pass; and (c) introducing into the mammal a second vector comprising: i) a polynucleotide encoding a rhesus monkey HER2/neu protein; and ii) a promoter operably linked to the polynucleotide.

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

The term "cassette" refers to the sequence of the present invention that contains the nucleic acid sequence which is to be expressed. The cassette is similar in concept to a cassette tape; each cassette has its own sequence. Thus by interchanging the cassette, the vector will express a different sequence. Because of the restriction sites at the 5' and 3' ends, the cassette can be easily inserted, removed or replaced with another cassette.

The term "vector" refers to some means by which DNA fragments can be introduced into a host organism or host tissue. There are various types of vectors including plasmid, virus (including adenovirus), bacteriophages and cosmids.

The term "first generation," as used in reference to adenoviral vectors, describes said adenoviral vectors that are replication-defective. First generation adenovirus vectors typically have a deleted or inactivated E1 gene region, and preferably have a deleted or inactivated E3 gene region.

The designation "pMRKAd5-rhHER2/neu" refers to a plasmid construct, disclosed herein, which comprises an Ad5 adenoviral genome deleted of the E1 and E3 regions. In this plasmid, the E1 region is replaced by a rhesus HER2/neu gene in an E1 parallel orientation, under the control of a human CMV promoter without intron A, followed by a bovine growth hormone polyadenylation signal.

The designation "MRKAd5-rhHER2/neu" refers to the virus generated from plasmid pMRKAD5-rhHER2/neu following removal of plasmid sequences by restriction and transfection into an E1-expressing cell line, such as Per.C6 or HEK 293.

The designation "pV1J-rhHER2/neu" refers to a plasmid construct disclosed herein comprising the human CMV immediate-early (IE) promoter and intron A, a full-length rhesus HER2/neu gene, a bovine growth hormone-derived polyadenylation and transcriptional termination sequences, and a minimal pUC backbone.

The term "first rhesus HER2/neu DNA sequence," as used interchangeably with the term "rhHER2#1," refers to the rhesus HER2/neu sequence as identified and isolated herein in EXAMPLE 1 and set forth in SEQ ID NO:1. This sequence was translated to determine the amino acid sequence of the "first rhesus HER2/neu protein," as set forth in SEQ ID NO:2.

The term "second rhesus HER2/neu DNA sequence," as used interchangeably with the term "rhHER2#2," refers to the rhesus HER2/neu sequence as identified and isolated herein in EXAMPLE 4 and set forth in SEQ ID NO:40. This DNA molecule was isolated from a different rhesus monkey than the DNA molecule described in EXAMPLE 1. This sequence was translated to deduce the amino acid sequence of the "second rhesus HER2/neu protein," as set forth in SEQ ID NO:41. Differences between the rhHER2#1 and rhHER2#2 nucleotide and amino acid sequences are detailed in FIG. 7.

The term "effective amount" means sufficient vaccine composition is introduced to produce the adequate levels of the polypeptide, so that an immune response results. One skilled in the art recognizes that this level may vary.

"Substantially free from other nucleic acids" means at least 90%, preferably 95%, more preferably 99%, and even more preferably 99.9%, free of other nucleic acids. As used interchangeably, the terms "substantially free from other nucleic acids," "substantially purified," "isolated nucleic acid" or "purified nucleic acid" also refer to DNA molecules which comprise a coding region for a rhesus HER2/neu protein that has been purified away from other cellular components. Thus, a rhesus HER2/neu DNA preparation that is substantially free from other nucleic acids will contain, as a percent of its total nucleic acid, no more than 10%, preferably no more than 5%, more preferably no more than 1%, and even more preferably no more than 0.1%, of non-rhesus HER2/neu nucleic acids. Whether a given rhesus HER2/neu DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

"Substantially free from other proteins" or "substantially purified" means at least 90%, preferably 95%, more preferably 99%, and even more preferably 99.9%, free of other proteins. Thus, a rhesus monkey HER2/neu protein preparation that is substantially free from other proteins will contain, as a percent of its total protein, no more than 10%, preferably no more than 5%, more preferably no more than 1%, and even more preferably no more than 0.1%, of non-rhesus monkey HER2/neu proteins. Whether a given rhesus monkey HER2/neu protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g. silver staining or immunoblotting.

As used interchangeably, the terms "substantially free from other proteins" or "substantially purified," or "isolated rhesus monkey HER2/neu protein" or "purified rhesus monkey HER2/neu protein" also refer to rhesus monkey HER2/neu protein that has been isolated from a natural source. Use of the term "isolated" or "purified" indicates that rhesus monkey HER2/neu protein has been removed from its normal cellular environment. Thus, an isolated rhesus monkey HER2/neu protein may be in a cell-free solution or placed in a different cellular environment from that in which it occurs naturally. The term isolated does not imply that an isolated rhesus monkey HER2/neu protein is the only protein present, but instead means that an isolated rhHER2/neu protein is substantially free of other proteins and non-amino acid material (e.g., nucleic acids, lipids, carbohydrates) naturally associated with the rhHER2/neu protein in vivo. Thus, a rhesus monkey HER2/neu protein that is recombinantly expressed in a prokaryotic or eukaryotic cell and substantially purified from this host cell which does not naturally (i.e., without intervention) express this rhHER2/neu protein is of course "isolated rhesus monkey HER2/neu protein" under any circumstances referred to herein. As noted above, a rhHER2/neu protein preparation that is an isolated or purified rhHER2/neu protein will be substantially free from other proteins and will contain, as a percent of its total protein, no more than 10%, preferably no more than 5%, more preferably no more than 1%, and even more preferably no more than 0.1%, of non-rhesus monkey HER2/neu proteins.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term "mammalian" refers to any mammal, including a human being.

The abbreviation "Ag" refers to an antigen.

The abbreviations "Ab" and "mAb" refer to an antibody and a monoclonal antibody, respectively.

BRIEF DESCRIPTION OF THE DRAWINGS

FIG. 1 shows the nucleotide sequence of the first rhesus monkey HER2/neu cDNA, as set forth in SEQ ID NO:1 (see EXAMPLE 1). The presence of an "R" at position 795 indicates that either an A or a G is located at that position.

FIG. 2 shows the predicted amino acid sequence of rhesus monkey HER2/neu protein, as set forth in SEQ ID NO:2. The amino acid sequence shown was deduced from the nucleotide sequence disclosed as SEQ ID NO:1.

FIG. 3 discloses the nucleotide sequences of oligonucleotide primers spanning the HER2/neu gene, which were used to generate a series of rhesus HER2/neu fragments by RT-PCR (see EXAMPLE 1). Columns marked "Forward" and "Reverse" state the location of the primers with respect to the published human HER2/neu sequence (Accession M11730). Primers disclosed as SEQ ID NOs:15 and 16 were designed to mutate amino acid position 579 from K to A, to inactivate the tyrosine kinase activity of the translated protein. Primers 3388-3410 and 3410-3388 have a sequence with a C at position 15 and a G at position 10, respectively, which code for Ser (AGC). In contrast, the Rhesus HER2/neu sequence has a T at that position, coding again for Ser (AGT). These primers were used for sequencing, but not for cloning purposes. For SEQ ID NOs:11 and 19, sequence priming on rhHER2/neu is underlined.

FIG. 4 shows the sequences of RT-PCR primers used to construct the full-length rhesus HER2/neu clone (see EXAMPLE 2). The first column lists the reaction number corresponding to the reactions discussed in EXAMPLE 2. Each row depicts a set of forward and reverse primers used to generate the clones listed in column 4. Nomenclature for the clones indicates both the vector used for cloning (BS or CR for pBluescript or pCRII, respectively) and the location of the sequence relative to the published human HER2/neu sequence (listed as numbers).

FIG. 5 shows the nucleotide sequence of the second rhesus monkey HER2/neu cDNA, as set forth in SEQ ID NO:40 (see EXAMPLE 4). The presence of an "R" within the nucleotide sequence indicates that either an "A" or a "G" is located at that position. The presence of a "Y" within the sequence indicates that a "C" or a "T" is located at that position. Nucleotide bases that are different from the corresponding bases of the first rhesus HER2/neu (SEQ ID NO:1) are bold and underlined.

FIG. 6 shows the predicted amino acid sequence of the second rhesus monkey HER2/neu protein, as set forth in SEQ ID NO:41 (see EXAMPLE 4). The amino acid sequence shown was deduced from the nucleotide sequence disclosed as SEQ ID NO:40. The "X" at position 517 indicates that a "Q" (Gln) or an "R" (Arg) may be present at that position. The "X" at position 647 indicates that a "K" (Lys) or an "R" (Arg) may be present at that position. The "X" at position 1075 indicates that an "R" (Arg) or a "Q" (Gln) may be present at that position.

FIG. 7 details the specific mutations present in the second rhesus HER2/neu DNA and protein sequences (RhHER2#2, SEQ ID NOs:40 and 41 ) as compared to the first rhesus HER2/neu DNA and protein sequences (RhHER2#1, SEQ ID NOs:1 and 2). The first column in each table lists the position of nucleotides that are different between RhHER2

2 and RhHER2#1. The second column in each table list the number of specific clones carrying HER2/neu fragments that were isolated and used to determine the sequence of RhHER2#1 and RhHER2#2, respectively. The third column in each table shows the sequence of the codon in which the differences occur, with dissimilar nucleotides highlighted. Below the codons are the one-letter amino acid symbols for the resulting amino acids, highlighted in gray.

DETAILED DESCRIPTION OF THE INVENTION

The gene encoding the HER2/neu tumor-associated antigen is commonly associated with the development of epithelial-derived human carcinomas. The present invention relates to compositions and methods to elicit or enhance immunity to the protein product expressed by the HER2/neu tumor-associated antigen, wherein aberrant HER2/neu expression is associated with the carcinoma or its development. Association of aberrant HER2/neu expression with a carcinoma does not require that the HER2/neu protein be expressed in tumor tissue at all timepoints of its development, as abnormal HER2/neu expression may be present at tumor initiation and not be detectable late into tumor progression.

To this end, polynucleotides encoding rhesus monkey HER2/neu are provided. The molecules of the present invention may be used in a recombinant adenovirus vaccine to provide effective immunoprophylaxis against epithelial-derived carcinomas through cell-mediated immunity. When directly introduced into a vertebrate in vivo, the invention polynucleotides induce the expression of encoded proteins within the animal, including mammals such as primates, dogs and humans.

The present invention relates to an isolated nucleic acid molecule (polynucleotide) comprising a sequence of nucleotides which encodes mRNA that expresses a novel rhHER2/neu protein as set forth in SEQ ID NO:2. The present invention also relates to an isolated nucleic acid molecule comprising a sequence of nucleotides which encodes mRNA that expresses a novel rhHER2/neu protein as set forth in SEQ ID NO:41. The nucleic acid molecules of the present invention are substantially free from other nucleic acids.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecules of the present invention may also include a ribonucleic acid molecule (RNA). For most cloning purposes, DNA is a preferred nucleic acid.

A preferred DNA molecule of the present invention comprises the nucleotide sequence disclosed herein as SEQ ID NO:1, shown in FIG. 1, which encodes the rhesus HER2/neu protein shown in FIG. 2 and set forth as SEQ ID NO:2. This rhHER2/neu nucleic acid molecule was identified through RT-PCR as described in detail in EXAMPLE 1. The presence of an "R" at position 795 of SEQ ID NO:1 indicates that clones isolated from the first rhesus monkey comprised either an A or a G at that position. A nucleic acid molecule isolated from the first rhesus monkey and comprising an "A" at position 795 is designated herein SEQ ID NO:42. A nucleic acid molecule isolated from the first rhesus monkey and comprising a "G" at position 795 is designated herein SEQ ID NO:43.

A second preferred DNA molecule comprises the nucleotide sequence disclosed herein as SEQ ID NO:40, shown in FIG. 5, which encodes the rhesus HER2/neu protein shown in FIG. 6 and set forth as SEQ ID NO:41. The isolated cDNA clones, associated vectors, hosts, recombinant subcellular fractions and membranes, and the expressed and mature forms of rhHER2/neu are useful for the development of a cancer vaccine.

The present invention also includes biologically active fragments or mutants of SEQ ID NO:1 or SEQ ID NO:40, which encode mRNA expressing novel rhHER2/neu proteins. Any such biologically active fragment and/or mutant will encode either a protein or protein fragment which at least substantially mimics the pharmacological properties of the rhHER2/neu protein, including but not limited to the rhHER2/neu proteins as set forth in SEQ ID NO:2 and SEQ ID NO:41. Any such polynucleotide includes but is not necessarily limited to: nucleotide substitutions, deletions, additions, amino-terminal truncations and carboxy-terminal truncations. The mutations of the present invention encode mRNA molecules that express a functional rhHER2/neu protein in a eukaryotic cell so as to be useful in cancer vaccine development.

This invention also relates to synthetic DNA that encodes the rhHER2/neu protein where the nucleotide sequence of the synthetic DNA differs significantly from the nucleotide sequence of SEQ ID NO:1 and SEQ ID NO:40, but still encodes the same rhHER2/neu protein as SEQ ID NO:2 or SEQ ID NO:41. Such synthetic DNAs are intended to be within the scope of the present invention.

Therefore, the present invention discloses codon redundancy that may result in numerous DNA molecules expressing an identical protein. For purposes of this specification, a sequence bearing one or more replaced codons will be defined as a degenerate variation. Also included within the scope of this invention are mutations either in the DNA sequence or the translated protein that do not substantially alter the ultimate physical properties of the expressed protein. For example, substitution of valine for leucine, arginine for lysine, or asparagine for glutamine may not cause a change in the functionality of the polypeptide.

It is known that DNA sequences coding for a peptide may be altered so as to code for a peptide that has properties that are different than those of the naturally occurring peptide. Methods of altering the DNA sequences include but are not limited to site directed mutagenesis. Examples of altered properties include but are not limited to changes in the affinity of an enzyme for a substrate or receptor for a ligand.

Included in the present invention are DNA sequences that hybridize to SEQ ID NO:1 or SEQ ID NO:40 under stringent conditions. By way of example, and not limitation, a procedure using conditions of high stringency is as follows: Prehybridization of filters containing DNA is carried out for 2 hours to overnight at 65° C. in buffer composed of 6×SSC, 5× Denhardt's solution, and 100 μg/ml denatured salmon sperm DNA. Filters are hybridized for 12 to 48 hrs at 65° C. in prehybridization mixture containing 100 μg/ml denatured salmon sperm DNA and 5-20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook et al., *Molecular Cloning: A Laboratory Manual*; Cold Spring Harbor Laboratory, Cold Spring Harbor, N.Y., 1989 which is hereby incorporated by reference. In addition to the foregoing, other conditions of high stringency which may be used are well known in the art.

A preferred aspect of the present invention is a substantially purified form of a rhesus monkey HER2/neu protein which comprises a sequence of amino acids as disclosed in FIG. 2 (SEQ ID NO:2).

Another preferred aspect of the present invention is a substantially purified form of a rhesus monkey HER2/neu protein which comprises a sequence of amino acids as disclosed in FIG. 6 (SEQ ID NO:41).

This invention also relates to various functional domains of rhHER2/neu, such as the extracellular domain and the intracellular domain, and to hybrid molecules comprising at least one of these sequences.

The present invention also includes biologically active fragments and/or mutants of a rhHER2/neu protein, comprising the amino acid sequence as set forth in SEQ ID NO:2 or SEQ ID NO:41, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for cancer vaccine development.

The rhesus monkey HER2/neu proteins of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also relates to rhHER2/neu fusion constructs, including but not limited to fusion constructs which express a portion of the rhesus HER2/neu protein linked to various markers, including but in no way limited to GFP (Green fluorescent protein), the MYC epitope, GST, and Fc. Any such fusion construct may be expressed in the cell line of interest and used to screen for modulators of the rhesus HER2/neu protein disclosed herein.

The present invention further relates to recombinant vectors that comprise the substantially purified nucleic acid molecules disclosed throughout this specification. These vectors may be comprised of DNA or RNA. For most cloning purposes, DNA vectors are preferred. Typical vectors include plasmids, modified viruses, bacteriophage, cosmids, yeast artificial chromosomes, and other forms of episomal or integrated DNA that can encode a rhHER2/neu protein. It is well within the purview of the skilled artisan to determine an appropriate vector for a particular gene transfer or other use.

An expression vector containing DNA encoding a rhHER2/neu protein may be used for expression of rhHER2/neu in a recombinant host cell. Expression vectors may include, but are not limited to, cloning vectors, modified cloning vectors, specifically designed plasmids or viruses. Also, a variety of bacterial expression vectors may be used to express recombinant rhHER2/neu in bacterial cells if desired. In addition, a variety of fungal cell expression vectors may be used to express recombinant rhHER2/neu in fungal cells. Further, a variety of insect cell expression vectors may be used to express recombinant protein in insect cells.

The present invention also relates to host cells transformed or transfected with vectors comprising the nucleic acid molecules of the present invention. Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines. Such recombinant host cells can be cultured under suitable conditions to produce rhHER2/neu or a biologically equivalent form.

As noted above, an expression vector containing DNA encoding a rhHER2/neu protein may be used for expression of rhHER2/neu in a recombinant host cell. Therefore, another aspect of this invention is a process for expressing a rhesus monkey HER2/neu protein in a recombinant host cell, comprising: (a) introducing a vector comprising the nucleic acid of as set forth in SEQ ID NO:1 or SEQ ID NO:40 into a suitable host cell; and, (b) culturing the host cell under conditions which allow expression of said rhesus monkey HER2/neu protein.

Following expression of rhHER2/neu in a host cell, rhHER2/neu protein may be recovered to provide rhHER2/neu protein in active form. Several rhHER2/neu protein purification procedures are available and suitable for use. Recombinant rhHER2/neu protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant rhHER2/neu protein can be separated from other cellular proteins by use of an immunoaffinity column made with monoclonal or polyclonal antibodies specific for full-length rhHER2/neu protein, or polypeptide fragments of rhHER2/neu protein.

The nucleic acids of the present invention may be assembled into an expression cassette that comprises sequences designed to provide for efficient expression of the protein in a human cell. The cassette preferably contains the full-length rhHER2/neu gene, with related transcriptional and translations control sequences operatively linked to it, such as a promoter, and termination sequences. In a preferred embodiment, the promoter is the cytomegalovirus promoter without the intron A sequence, although those skilled in the art will recognize that any of a number of other known promoters such as the strong immunoglobulin, or other eukaryotic gene promoters may be used. A preferred transcriptional terminator is the bovine growth hormone terminator, although other known transcriptional terminators may also be used. The combination of CMV-BGH terminator is particularly preferred.

In accordance with this invention, the rhesus HER2/neu expression cassette is inserted into a vector. The vector is preferably an adenoviral vector, although linear DNA linked to a promoter, or other vectors, such as adeno-associated virus or a modified vaccinia virus vector may also be used.

If the vector chosen is an adenovirus, it is preferred that the vector be a so-called first-generation adenoviral vector. These adenoviral vectors are characterized by having a non-functional E1 gene region, and preferably a deleted adenoviral E1 gene region. In some embodiments, the expression cassette is inserted in the position where the adenoviral E1 gene is normally located. In addition, these vectors optionally have a non-functional or deleted E3 region. It is preferred that the adenovirus genome used be deleted of both the E1 and E3 regions (ΔE1ΔE3). The adenoviruses can be multiplied in known cell lines which express the viral E1 gene, such as 293 cells, or PERC.6 cells, or in cell lines derived from 293 or PERC.6 cell which are transiently or stablily transformed to express an extra protein. For examples, when using constructs that have a controlled gene expression, such as a tetracycline regulatable promoter system, the cell line may express components involved in the regulatory system. One example of such a cell line is T-Rex-293; others are known in the art.

For convenience in manipulating the adenoviral vector, the adenovirus may be in a shuttle plasmid form. This invention is also directed to a shuttle plasmid vector which comprises a plasmid portion and an adenovirus portion, the adenovirus portion comprising an adenoviral genome which has a deleted E1 and optional E3 deletion, and has an inserted expression cassette comprising rhesus HER2/neu. In preferred embodiments, there is a restriction site flanking the adenoviral portion of the plasmid so that the adenoviral vector can easily be removed. The shuttle plasmid may be replicated in prokaryotic cells or eukaryotic cells.

In a preferred embodiment of the invention, the expression cassette is inserted into the pMRKAd5-HV0 adenovirus plasmid (See Emini et al., WO 02/22080, which is hereby incorporated by reference). This plasmid comprises an Ad5 adenoviral genome deleted of the E1 and E3 regions. The design of the pMRKAd5-HV0 plasmid was improved over prior adenovectors by extending the 5' cis-acting packaging region further into the E1 gene to incorporate elements found to be important in optimizing viral packaging, resulting in enhanced virus amplification. Advantageously, this enhanced adenoviral vector is capable of maintaining genetic stability following high passage propagation.

Standard techniques of molecular biology for preparing and purifying DNA constructs enable the preparation of the adenoviruses, shuttle plasmids, and DNA immunogens of this invention.

The vectors described above may be used in immunogenic compositions and vaccines for preventing the development of epithelial-derived carcinomas associated with aberrant HER2/neu expression and/or for treating existing cancers. To this end, one aspect of the instant invention is a method of preventing or treating cancer comprising administering to a mammal a vaccine vector comprising an isolated nucleic acid molecule, the isolated nucleic acid molecule comprising a sequence of nucleotides that encodes a rhesus monkey HER2/neu protein as set forth in SEQ ID NO:2 or SEQ ID NO:41.

In accordance with the method described above, the vaccine vector may be administered for the treatment or prevention of cancer in any mammal. In a preferred embodiment of the invention, the mammal is a human.

Further, one of skill in the art may choose any type of vector for use in the treatment and prevention method described. Preferably, the vector is an adenovirus vector or a plasmid vector. In a preferred embodiment of the invention, the vector is an adenoviral vector comprising an adenoviral genome with a deletion in the adenovirus E1 region, and an insert in the adenovirus E1 region, wherein the insert comprises an expression cassette comprising: (a) a polynucleotide encoding a rhesus monkey HER2/neu protein; and (b) a promoter operably linked to the polynucleotide.

The instant invention further relates to an adenovirus vaccine vector comprising an adenoviral genome with a deletion in the E1 region, and an insert in the E1 region, wherein the insert comprises an expression cassette comprising: (a) a polynucleotide encoding a rhesus monkey HER2/neu protein; and (b) a promoter operably linked to the polynucleotide.

In a preferred embodiment of this aspect of the invention, the adenovirus vector is an Ad 5 vector.

In another aspect, the invention relates to a vaccine plasmid comprising a plasmid portion and an expression cassette portion, the expression cassette portion comprising: (a) a polynucleotide encoding a rhesus monkey HER2/neu protein; and (b) a promoter operably linked to the polynucleotide.

In some embodiments of this invention, the recombinant adenovirus vaccines disclosed herein are used in various prime/boost combinations with a plasmid-based polynucleotide vaccine in order to induce an enhanced immune response. In this case, the two vectors are administered in a "prime and boost" regimen. For example the first type of vector is administered, then after a predetermined amount of time, for example, 1 month, 2 months, six months, or other appropriate interval, a second type of vector is administered. Preferably the vectors carry expression cassettes encoding the same polynucleotide or combination of polynucleotides. In the embodiment where a plasmid DNA is also used, it is preferred that the vector contain one or more promoters recognized by mammalian or insect cells. In a preferred embodiment, the plasmid would contain a strong promoter such as, but not limited to, the human CMV promoter. The rhesus HER2/neu gene or other gene to be expressed would be linked to such a promoter. An example of such a plasmid would be the mammalian expression plasmid VlJns as described (J. Shiver et. al. in *DNA Vaccines*, M. Liu et al. eds., N.Y. Acad. Sci., N.Y., 772:198-208 (1996), which is herein incorporated by reference).

As stated above, an adenoviral vector vaccine and a plasmid vaccine may be administered to a vertebrate as part of a single therapeutic regime to induce an immune response. To this end, the present invention relates to a method of protecting a mammal from cancer comprising: (a) introducing into the mammal a first vector comprising: i) a polynucleotide encoding a rhesus monkey HER2/neu protein; and ii) a promoter operably linked to the polynucleotide; (b) allowing a predetermined amount of time to pass; and (c) introducing into the mammal a second vector comprising: i) a polynucleotide encoding a rhesus monkey HER2/neu protein; and ii) a promoter operably linked to the polynucleotide.

In one embodiment of the method of protection described above, the first vector is a plasmid and the second vector is an adenovirus vector. In an alternative embodiment, the first vector is an adenovirus vector and the second vector is a plasmid.

The instant invention further relates to a method of treating a mammal suffering from an epithelial-derived carcinoma comprising: (a) introducing into the mammal a first vector comprising: i) a polynucleotide encoding a rhesus monkey HER2/neu protein; and ii) a promoter operably linked to the polynucleotide; (b) allowing a predetermined amount of time to pass; and (c) introducing into the mammal a second vector comprising: i) a polynucleotide encoding a rhesus monkey HER2/neu protein; and ii) a promoter operably linked to the polynucleotide.

In one embodiment of the method of treatment described above, the first vector is a plasmid and the second vector is an adenovirus vector. In an alternative embodiment, the first vector is an adenovirus vector and the second vector is a plasmid.

The amount of expressible DNA or transcribed RNA to be introduced into a vaccine recipient will depend partially on the strength of the promoters used and on the immunogenicity of the expressed gene product. In general, an immunologically or prophylactically effective dose of about 1 ng to 100 mg, and preferably about 10 µg to 300 µg of a plasmid vaccine vector is administered directly into muscle tissue. An effective dose for recombinant adenovirus is approximately $10^6$-$10^{12}$ particles and preferably about $10^7$-$10^{11}$ particles. Subcutaneous injection, intradermal introduction, impression though the skin, and other modes of administration such as intraperitoneal, intravenous, or inhalation delivery are also contemplated. It is also contemplated that booster vaccinations may be provided. Parentaeral administration, such as intravenous, intramuscular, subcutaneous or other means of administration with adjuvants such as interleukin 12 protein, concurrently with or subsequent to parenteral introduction of the vaccine of this invention is also advantageous.

The vaccine vectors of this invention may be naked, i.e., unassociated with any proteins, adjuvants or other agents which impact on the recipient's immune system. In this case, it is desirable for the vaccine vectors to be in a physiologically acceptable solution, such as, but not limited to, sterile saline or sterile buffered saline. Alternatively, it may be advantageous to administer an immunostimulant, such as an adjuvant, cytokine, protein, or other carrier with the vaccines or immunogenic compositions of the present invention. Therefore, this invention includes the use of such immunostimulants in conjunction with the compositions and methods of the present invention. An immunostimulant, as used herein, refers to essentially any substance that enhances or potentiates an immune response (antibody and/or cell-mediated) to an exogenous antigen. Said immunostimulants can be administered in the form of DNA or protein. Any of a variety of immunostimulants may be employed in conjunction with the vaccines and immunogenic compositions of the present inventions, including, but not limited to: GM-CSF, IFNα, tetanus toxoid, IL12, B7.1, LFA-3 and ICAM-1. Said immunostimulants are well-known in the art. Agents which assist in the cellular uptake of DNA, such as, but not limited to calcium ion, may also be used. These agents are generally referred to as transfection facilitating reagents and pharmaceutically acceptable carriers. Those of skill in the art will be able to determine the particular immunostimulant or pharmaceutically acceptable carrier as well as the appropriate time and mode of administration.

Any of a variety of procedures may be used to clone rhHER2/neu. These methods include, but are not limited to, (1) a RACE PCR cloning technique (Frohman et al., *Proc. Natl. Acad. Sci. USA* 85: 8998-9002 (1988)). 5' and/or 3' RACE may be performed to generate a full-length cDNA sequence. This strategy involves using gene-specific oligonucleotide primers for PCR amplification of rhHER2/neu cDNA. These gene-specific primers are designed through identification of an expressed sequence tag (EST) nucleotide sequence which has been identified by searching any number of publicly available nucleic acid and protein databases; (2) direct functional expression of the rhHER2/neu cDNA following the construction of a rhHER2/neu-containing cDNA library in an appropriate expression vector system; (3) screening an rhHER2/neu-containing cDNA library constructed in a bacteriophage or plasmid shuttle vector with a labeled degenerate oligonucleotide probe designed from the amino acid sequence of the rHER2/neu protein; (4) screening an rhHER2/neu-containing cDNA library constructed in a bacteriophage or plasmid shuttle vector with a partial cDNA encoding the rhHER2/neu protein. This partial cDNA is obtained by the specific PCR amplification of rhHER2/neu DNA fragments through the design of degenerate oligonucleotide primers from the amino acid sequence known for other growth factor receptors which are related to the rhHER2/neu protein; (5) screening a rhHER2/neu-containing cDNA library constructed in a bacteriophage or plasmid shuttle vector with a partial cDNA or oligonucleotide with homology to a mammalian rhHER2/neu protein. This strategy may also involve using gene-specific oligonucleotide primers for PCR amplification of rhHER2/neu cDNA identified as an EST as described above; or (6) designing 5' and 3' gene specific oligonucleotides using SEQ ID NO: 1 or SEQ ID NO:40 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding rhHER2/neu.

It is readily apparent to those skilled in the art that other types of libraries, as well as libraries constructed from other cell types-or species types, may be useful for isolating a rhHER2/neu-encoding DNA or a rhHER2/neu homologue. Other types of libraries include, but are not limited to, cDNA libraries derived from other cells.

It is also readily apparent to those skilled in the art that suitable cDNA libraries may be prepared from cells or cell lines which have rhHER2/neu activity, such as various epithelial-derived cells. The selection of cells or cell lines for use in preparing a cDNA library to isolate a cDNA encoding rhHER2/neu may be done by first measuring cell-associated rhHER2/neu activity using any known assay available for such a purpose.

Preparation of cDNA libraries can be performed by standard techniques well known in the art. Well known cDNA library construction techniques can be found for example, in Sambrook et al., *Molecular Cloning: A Laboratory Manual*; Cold Spring Harbor Laboratory, Cold Spring Harbor, N.Y., 1989. Complementary DNA libraries may also be obtained from numerous commercial sources, including but not limited to Clontech Laboratories, Inc. (Palo Alto, Calif.) and Stratagene (La Jolla, Calif.).

The DNA molecules, RNA molecules, and recombinant protein of the present invention may be used to screen and measure levels of rhHER2/neu. The recombinant proteins, DNA molecules, and RNA molecules lend themselves to the formulation of kits suitable for the detection and typing of rhHER2/neu. Such a kit would comprise a compartmentalized carrier suitable to hold in close confinement at least one container. The carrier would further comprise reagents such as recombinant rhHER2/neu or anti-rhHER2/neu antibodies suitable for detecting rhHER2/neu. The carrier may also contain a means for detection such as labeled antigen or enzyme substrates or the like.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Isolation of the Rhesus HER2/neu cDNA by RT-PCR

Molecular procedures were performed following standard procedures well known in the art (See; e.g., Ausubel et. al. *Short Protocols in Molecular Biology*, F. M., -2$^{nd}$. ed., John Wiley & Sons, (1992) and Sambrook et al., *Molecular Cloning, A Laboratory Manual*, 2$^{nd}$ ed., Cold Spring Harbor Laboratory Press (1989), which are hereby incorporated by reference).

HER2/neu nucleotide sequences from human, hamster, dog, and rat were aligned to identify highly conserved regions of the HER2/neu DNA. Based on the sequence comparison, oligonucleotide primers spanning the HER2/neu gene were designed for amplification of the rhesus HER2/neu cDNA by reverse transcriptase polymerase chain reaction (RT-PCR), described below. (see FIG. 3).

Colon biopsies from two different Rhesus monkeys (*macaca mulatta*) were obtained from Dr. Willem Collignon (Biomedical Primate Research Centre (BPRC), Rijswijk, The Netherlands). RNA was extracted and purified from each colon biopsy using the UltraSPec-II RNA isolation system (Biotecx, Houston, Tex.) according to the manufacturer's instructions. To isolate the rhesus HER2/neu gene, RT-PCR amplification products covering the entire HER2/neu sequence were generated from total RNA isolated from a single rhesus monkey.

To perform the reverse transcription step, total RNA samples were reverse transcribed using the Superscript One-Step RT-PCR Amplification Kit for Long Templates (Life Technologies; Carlsbad, Calif.) according to the manufacturer's instructions. Typically, 0.5-2.0 μg RNA were combined with the reverse transcriptase enzyme and the appropriate buffer in a 50 μl reaction volume. Samples were incubated at 45° C. for 30 min, followed by a 2 minute incubation at 94° C.

Using the resulting cDNA templates, PCR amplifications were performed using different combinations of forward and reverse primers (see FIG. 3). PCR was carried out in a Perkin Elmer 2400 thermocycler (Perkin Elmer, Inc., Wellesley, Mass.). Cycling conditions consisted of 35 cycles of an initial denaturation step of 94° C. for 15 sec, followed by a primer annealing step and concluding with an extension step. The primer annealing step consisted of incubation for 50 sec at a temperature ranging from (50° C.–51° C.), depending on the primer sequence. The extension step consisted of an incubation at 68° C. for a length of time ranging from (80 sec-100 sec), depending on the expected length of the amplification product. The above 35 cycles were followed by an extensive elongation step of 7 min at 72° C.

Amplification products were gel-purified using the QIAquick PCR Purification Kit (Qiagen, Hilden, Germany) and sequenced with the same primers used for amplification. Sequencing reactions were carried out through Big Dye Terminator chemistry, using the Cycle Sequencing Ready Reaction Kit (Applied Biosystems, Foster City, Calif.). Readings were performed using an ABI Prism 377 DNA sequencer (Applied Biosystem).

Data acquired by sequencing the different amplification products, which encompass the entire HER2/neu coding region, identified the rhesus HER2/neu sequence, disclosed herein as SEQ ID NO:1 (hereinafter "first rhesus HER2 nucleotide sequence" or "rhHER2#1," see FIG. 1). The presence of an "R" at position 795 of SEQ ID NO:1 indicates that clones isolated from the first rhesus monkey comprised either an A or a G at that position. A nucleic acid molecule isolated from the first rhesus monkey and comprising an "A" at position 795 is designated herein SEQ ID NO:42. A nucleic acid molecule isolated from the first rhesus monkey and comprising a "G" at position 795 is designated herein SEQ ID NO:43. The single nucleotide change at position 795 of SEQ ID NO:1, based on DNA isolated from the first rhesus monkey, did not affect the resulting amino acid sequence of the HER2/neu protein, which is disclosed herein as SEQ ID NO:2 (see FIG. 2).

Amplification products derived from the above RT-PCR reactions were cloned into either vector BlueScript ks(+) or pCRII, referred to herein as BS or CR, respectively. The resulting clones were sequenced to confirm the rhHER2/neu nucleotide sequence obtained by direct sequencing of amplification products and used to assemble the complete rhesus HER2/neu cDNA sequence.

EXAMPLE 2

Assembly of the Complete HER2/neu cDNA Sequence

A series of clones obtained from the first rhesus monkey were constructed and assembled by PCR to generate the complete rhesus HER2/neu cDNA. First, four RT-PCR amplification products spanning the 5' end of the rhesus HER2/neu gene were generated as described in EXAMPLE 1. The PCR-amplified fragments from the above clones were cloned into either BS or CR, as indicated in FIG. 4 (Reactions 1-4). Sequence analysis of several clones confirmed that the cloned sequences were the same as sequences obtained from the RT-PCR fragments.

The overlapping amplication products described above were ligated in a 100 μl PCR reaction in which the following components were combined: 0.1-1.0 pmol of each of the above fragments, Pfu polymerase (Stratagene, La Jolla, Calif.) and the appropriate buffer. Samples were subjected to an initial amplification cycle consisting of 30 sec at 95° C., followed by 4 min at 72° C.

The resulting ligation product was amplified again with the PmeI_SwaI_RBS_1-16 (SEQ ID NO:11) and 1895-1876 (SEQ ID NO:10) primers using Pfu polymerase and the appropriate buffer with the following thermal profile: 95° C. for 30 sec, 58° C. for 30 sec and 72° C. for 180 sec (30 cycles). The PCR product thus obtained was gel purified and cloned into pCRII vector to generate clone #1_CR_ 1-1895.7(–) (in the anti-clockwise orientation). Sequence analysis of several clones confirmed the identity of the cloned sequence.

Colon RNA from the first rhesus monkey was used to generate an additional PCR fragment by RT-PCR, essentially as described above. Oligonucleotide primers used for this purpose were as follows: 1558-1583 (SEQ ID NO:12) and 2798-2776 (SEQ ID NO:13) (Reaction 6, FIG. 4). This fragment, located in the center portion of the HER2/neu gene, was used as a template for further amplification, without cloning.

Primers were then designed to PCR-amplify this region from bp 1621 to bp 2277 (FIG. 4, Reactions 7, SEQ ID NOs: 14, 15) and from bp 2239 to 2798 (FIG. 4, Reaction 8, SEQ ID NOs: 16 and 13). The resulting products were cloned into the pCRII vector. In order to inactivate the tyrosine kinase activity of the protein, primers were designed to mutate amino acid position 579 from K to A (SEQ ID NOs:15 and 16). Sequence analysis of several clones confirmed the identity of the cloned sequences.

Colon RNA from the first rhesus monkey was used to generate an additional PCR fragment by RT-PCR, essentially as described above. Oligonucleotide primers used for this purpose were as follows:2356-2378 (SEQ ID NO:17) and 4166-4145 (SEQ ID NO:18) (FIG. 4, Reaction 9). The resulting product was cloned into the pCRII vector. Sequence analysis confirmed the identity of the cloned sequences.

DNA fragments were PCR amplified from the three above clones using the following primers: 1621-1644 (SEQ ID NO 14) and 2277-K753-2248 (SEQ ID NO 15) with template #1_CR__1621-2277.2; 2239-K756-2248 (SEQ ID NO 16) and 2798-2776 (SEQ ID NO 13) with template #1_CR__2239-2798.4; 2356-2378 (SEQ ID NO 17) and SalI__3768-3746 (SEQ ID NO 19) with template #1_CR__2356-4169.2. The three products were assembled by PCR as described above. The resulting ligation product was amplified using the following primers: 1621-1644 (SEQ ID NO:14) and SalI__3768-3746' (SEQ ID NO:19) and cloned into pCRII vector in the clockwise orientation, generating clones #1-CR__1621-3768.8 (hereinafter clone 10.8) and #1-CR__1621-3768.12 (hereinafter clone 10.12) (FIG. 4, Reactions 10). Sequencing revealed that clone 10.12 had a mutation around position 3686 in the 3' region. Similarly, clone 10.8 had a mutation around position 2666. A wild type sequence was generated by replacing a 508 bp BstEII-SalI fragment from clone 10.12 with the corresponding region from clone 10.8, which did not include mutations in this region. The resulting clone was named #1-CR__1621-3768.128.

A PmlI-XbaI fragment from clone #1_CR__1621__3768.128(+) was cloned into the PmlI-SpeI sites of clone #1_CR__1__1895.7(-). The resulting plasmid, which contains the entire rhesus HER2/neu coding sequence, was named #1_CR__1-3768(-). Sequence analysis confirmed the identity of the sequence.

EXAMPLE 3

Immunogens

For gene transduction and immunization studies, the rhHER2/neu coding region was excised from #1_CR__1-3768(-) by digestion with PmeI and SalI and inserted into the EcoRV and SalI sites of mammalian expression plasmid pV1J_nsA (Montgomery et al., DNA Cell Biol. 12(9): 777-83 (1993)), generating pV1J-rh-HER2/neu.

For adenovirus vector construction, the rhHER2/neu-encoding sequence was excised from #1_CR__1-3768(-) by digestion with PmeI and SalI and cloned into the corresponding site of the ppolyMRKAd5ΔE1 shuttle plasmid, generating pMRKAd5ΔE1-rhHER2/neu. Shuttle vector pMRKAd5ΔE1 contains Ad5 sequences from b.p. 1 to b.p. 450 and from b.p. 3511 to b.p. 5798 with an expression cassette containing human cytomegalovirus (HCMV) promoter (without intron A) and bovine growth hormone polyadenylation signal. The plasmid was recombined with the adenoviral backbone vector pMRKAd5HVO, which contains all Ad5 sequences except those encompassing the E1 and E3 regions, using E. coli BJ5183 cells (Chartier et al., J. Virol. 70: 4805-10 (1996)).

For vector production, pMRKAd5-rhHER2/neu was linearized by digestion with PacI and transfected in PerC.6 cells using Lipofectamine (Life Technologies, Rockville, Md.). 5-6 viral passages were performed to amplify viral titer and a large viral amplification was carried out with a final production of $1.3 \times 10^{12}$ physical particles (pp). No genome rearrangements were detectable in the viral genome purified from the amplified vector, as indicated by restriction fragment length polymorphism (RFLP) analysis. The expected DNA fragments were observed both in the viral genome and in the control pMRKAd5-HER2/neu plasmid, restricted in parallel.

EXAMPLE 4

Isolation of HER2/neu-encoding DNA from a Second Rhesus Monkey

A similar sequencing analysis of RT-PCR products was performed using colon RNA from a second rhesus monkey (see EXAMPLE 1). Data acquired by sequencing many different amplification products encompassing the whole gene identified a second rhesus HER2/neu sequence, disclosed herein as SEQ ID NO:40, (hereinafter "second rhesus HER2 nucleotide sequence" or "rhHER2#2," see FIG. 5), with the deduced amino acid sequence disclosed herein as SEQ ID NO:41 (hereinafter "second rhesus HER2 amino acid sequence," see FIG. 6).

As in EXAMPLE 1, amplification products were generated by RT-PCR of total colon RNA from the second rhesus monkey using primers spanning the HER2/neu gene (see FIG. 3). The resulting amplification products were gel-purified and sequenced. Additionally, these products were cloned into either the BS or the CR vector. DNA sequencing analysis of the resulting clones confirmed the rhHER2/neu nucleotide sequences obtained by direct sequencing of amplification products.

Eight differences were detected between rhHER2#1 and rhHER2#2 (for details, see FIG. 7). Five of these mutations introduce an amino acid change in the protein as compared to the first rhesus HER2 amino acid sequence (SEQ ID NO:2). Of note, three of these mutations do not produce amino acid changes in the rhHER2#2 protein as compared with the rhHER2#1 protein.

EXAMPLE 5

Immunization of Rhesus Macaques with rhHER2/neu

In order to assess the efficiency of immunization of Rhesus macaques (*Macaca mulatta*) with the rhesus homologues of the human tumor antigen HER2/neu, which is expressed in colorectal carcinomas, immunization studies were performed at the Biomedical Primate Research Centre (BPRC), Rijswijk (The Netherlands). The studies were designed to evaluate both B and T cell responses to immunization with the rhesus HER2/neu antigen.

In a first study, one group of monkeys (4 rhesus monkeys total; 2 males and 2 females) were immunized with a plasmid DNA vector or an adenovirus vector expressing the rhesus homologue of the human tumor antigen HER2/neu (pV1J-rhHER2). For priming, animals were vaccinated intramuscularly (i.m.) with plasmid DNA at weeks 0, 4, 8, 12, and 16, by injection of DNA followed by electrical stimulation. The DNA was injected as a 1 ml solution (split over 2 sites with 0.5 ml/site) containing 5 mg pV1J-rhHER2 plasmid DNA for animals weighing 2-5 kilos. Animals are injected under anesthesia (mixture of ketamine/xylazine).

For electrostimulation, 2 trains of 100 square bipolar pulses (1 sec each), were delivered every other second for a total treatment time of 3 sec. The pulse length was 2 msec/phase with a pulse frequency and amplitude of 100 Hz and 100 mA (constant current mode), respectively.

The same group of animals was boosted by i.m. injection of Adenovirus 5 (Ad5) expressing rhesus HER2/neu. A ΔE1-ΔE3, "first generation" Adenovirus (P2 level) was used. A total amount of 10 exp11 viral particles (vp) were injected at week 24 and 28.

A further boosting was carried out by i.m. injection of 10exp11 viral particles (vp) of Adenovirus 24 (Ad24) expressing rhesus HER2/neu at weeks 36 and 40. Ad24 was chosen because neutralizing antibodies induced by Ad5 injection do not interfere with Ad24 infection.

To measure the immune response to HER2/neu induced by the above immunization protocol, blood samples were collected every four weeks for a total duration of one year. The HER2-specific cell mediated immune response was measured by IFNγ ELISPOT assay. The number of IFN-γ-secreting anti-rhesus HER2 T cells was determined by ELISPOT on PBMC using pools of peptides. Three hundred and eleven peptides, each 15 amino acids long, overlapping by 11 residues and spanning the entire rhesus protein sequence, were combined into eleven pools indicated with alphabetical letters from A to K (from N- to C-terminus). The frequency of IFN-γ producing PBMC was calculated as the average value of spots derived from duplicates at two different cell concentrations. Values were expressed as the number of spot forming colonies (SFC)/$10^6$ total PBMC, minus the background values determined in the absence of peptides (typically less than 10 SpC/$10^6$ total spleen cells). Calculated results indicate that all four monkeys showed a detectable cell-mediated response, as measured by IFN-γ ELISPOT.

Reactivity was confirmed and typed by IFN-γ+ intracellular staining (ICS), which measured the frequency of $CD4^+$ or $CD8^+$ T-cell secreting IFN-γ. $CD3^+$ lymphocytes were collected by simultaneously gating on $CD3^+$ events and small lymphocytes. Values higher than 0.1% were considered positive. A positive value of 0.19 (CD8+) was obtained for monkey R1504 for pool J. No detectable anti-rhHER2 antibodies titres (>200) were detected.

In summary, i.m. injection of plasmid DNA expressing rhesus HER2/neu was effective in breaking tolerance and inducing a detectable cell-mediated immune response against rhHER2/neu in rhesus monkeys

EXAMPLE 6

Immunization of Rhesus Macaques with Rhesus Homologs of Human Tumor-Associated Antigens A second series of immunization studies were performed at the Biomedical Primate Research Centre (BPRC), Rijswijk (The Netherlands) in order to assess the efficiency of immunization of Rhesus macaques (*macaca mulatta*) with rhesus homologues of the human tumor antigens HER2/neu, Ep-CAM and CEA, which are all expressed in colorectal carcinomas. Protocols were designed to evaluate both B and T cell responses to these tumor antigens in combination.

In this study, a second group of 4 rhesus monkeys (2 males and 2 females) were immunized with a mixture of three plasmid DNA vectors expressing the rhesus homologues of human tumor antigens Ep-CAM (pV1J-rhHER2), CEA (pV1J-rhCEA), and HER2/neu (pV1J-rhEpCAM).

Animals were primed by i.m. injection of plasmid DNA at weeks 0, 4, 8, 12, and 16, followed by electrostimulation. The DNA injection consisted of a 1 ml solution (split over 2 sites with 0.5 ml/site) containing 6 mg plasmid DNA (2 mg for each of the three TAAs) for animals weighing 2-5 kilos. Animals were injected under anesthesia (mixture of ketamine/xylazine).

For electrostimulation, 2 trains of 100 square bipolar pulses (1 sec each), were delivered every other second for a total treatment time of 3 sec. The pulse length was 2 msec/phase with a pulse frequency and amplitude of 100 Hz and 100 mA (constant current mode), respectively.

The same group of animals was boosted by injection of a mixture of three Ad5-expressing rhesus HER2/neu (Ad5-rhHER2), rhesus CEA (Ad5-rhCEA) and rhesus EpCAM (Ad5-rhEpCAM). A total amount of 3×10exp11 viral particles (vp), were injected i.m. at weeks 23 and 27 (1×10exp11 vp for each of the three viruses).

A further boosting was carried out by i.m. injection of a mixture of three Ad24-expressing rhesus HER2/neu (Ad24-rhHER2), rhesus CEA (Ad24-rhCEA) and rhesus EpCAM (Ad24-rhEpCAM). A total amount of 3×10exp11 viral particles (vp), were injected i.m. at weeks 36 and 40 (1×10exp11 vp for each of the three viruses).

To measure the immune response to HER2/neu using the above immunization protocol, blood samples were collected every four weeks for a total duration of one year. The cell mediated immune response was measured by IFN-γ+ ELISPOT and intracellular staining, whereas the humoral response was measured by ELISA.

Monkeys RI449 and RI519 showed a detectable HER2-specific cell-mediated response, as measured by IFN-γ ELISPOT analysis. A similar analysis did not detect any response against rhCEA and rhEpCAM. No detectable anti-rheHER2 antibodies titres (>200) were detected.

In a third study, 4 rhesus monkeys were immunized with a mixture of Ad5-rhHER2, Ad5-rhCEA and Ad5-rhEpCAM by i.m. injection of Ad5 derivatives at weeks 0, 2 and 4. A 1 ml solution (split over 2 sites with 0.5 ml/site) containing 3×10exp11 vp (10exp11 for each of the three Ad5 virus) was administered to animals weighing 2-5 kilos, under anesthesia (mixture of ketamine/xylazine).

The same group of animals was boosted at weeks 24, 26 and 28 by i.m. injection of a mixture of Ad24-rhHER2, Ad24-rhCEA and Ad24-rhEpCAM (a total amount of 3×10exp11 vp, 10exp11 vp for each of the three viruses). The cell mediated response was measured by IFNγ ELISPOT assay. For monkeys RI514 and RI496, reactivity was typed by IFN-Yγ+ intracellular staining. Three out of four monkeys showed a detectable response. In addition, anti-rhHER2 antibody titres ranging from 200 to 500 were detected in the three monkeys where a cell-mediated response was measured.

This immunization protocol was also effective in breaking tolerance and inducing anti-rhCEA cell-mediated and humoral immune responses. Monkey RI514 showed a measurable cell mediated response by IFN-γ ELISPOT analysis. Intracellular staining confirmed this response. The same monkey also showed anti-rhCEA antibodies titres ranging from 500 to 1000. By contrast, a similar analysis did not detect any response against rhEpCAM.

In summary, the immunization protocol discussed above was effective in inducing a specific immune response against rhHER2/neu and rhCEA in rhesus monkeys.

What is claimed is:

1. An isolated nucleic acid molecule comprising a sequence of nucleotides that encodes a rhesus monkey HER2/neu protein as set forth in SEQ ID NO:2 or SEQ ID NO:41.

2. The isolated nucleic acid molecule of claim 1 wherein the nucleic acid is DNA.

3. The isolated nucleic acid molecule of claim 1 wherein the sequence of nucleotides comprises the sequence of nucleotides set forth in SEQ ID NO:1, SEQ ID NO:40, SEQ ID NO:42, or SEQ ID NO:43.

4. A vector comprising the nucleic acid molecule of claim 1.

5. A host cell comprising the vector of claim 4.

6. A process for expressing a rhesus HER2/neu protein in a recombinant host cell, comprising:
   (a) introducing a vector comprising the nucleic acid of claim 1 into a suitable host cell; and,
   (b) culturing the host cell under conditions which allow expression of said rhesus HER2/neu protein.

7. An isolated and purified rhesus HER2/neu polypeptide comprising the sequence of amino acids as set forth in SEQ ID NO:2 or SEQ ID NO:41.

* * * * *

SEQUENCE LISTING

<160> NUMBER OF SEQ ID NOS: 43

<210> SEQ ID NO 1
<211> LENGTH: 3768
<212> TYPE: DNA
<213> ORGANISM: Rhesus Monkey

<400> SEQUENCE: 1

```
atggagctgg cggcctggta ccgctggggg ctcctcctcg ccctcttgcc ccccggagct      60
gcgggcaccc aagtgtgcac cggcacagac atgaagctgc ggctccctgc cagtcccgag     120
acccacctgg acatgctccg ccacctctac cagggctgcc aggtggtgca gggtaacctg     180
gaactcacct acctgcccac caatgccagc ctctccttcc tgcaggatat ccaggaggtg     240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacctgctga caataccac ccctgtcaca ggggcctccc caggaggcct gcgggagctg     420
cagcttcgaa gcctcacaga gatcttgaaa ggagggtct tgatccagcg gaacccccag     480
ctctgctacc aggacacgat tttgtggaag acatcttcc ataagaacaa ccagctggct     540
ctcacactga tcgacaccaa ccgctctcgg cctgccacc cctgttctcc agtgtgtaag     600
ggctcccgct gctgggggaga gagttctgag gattgtcaga gcctgacgcg cactgtctgt     660
gccggtggct gtgcccgctg caaggggcca ctgcccactg actgctgcca tgagcagtgt     720
gctgccggct gcacgggccc caagcactct gactgcctgg cctgcctcca cttcaaccac     780
agcggcatct gtgarctgca ctgcccagcc tggtcacct acaacacaga cacctttgag     840
tccatgccca accccgaggg ccggtataca ttcggcgcca gctgtgtgac tgcctgtccc     900
tacaactacc tttctacgga cgtgggatcc tgcaccctcg tctgccccct gcacaaccaa     960
gaggtgacag cggaggacgg aacacagcga tgtgagaagt gcagcaagcc ctgtgcccga    1020
gtgtgctatg gtctgggcat ggagcacttg cgagaggtga gggcggtcac cagtgccaat    1080
atccaggagt ttgctggctg caagaagatc tttgggagct tggcatttct gccagagagc    1140
tttgatggcg acccagcctc caacaccgcc ccgcttcagc cggagcagct ccgagtgttt    1200
gagactctgg aagagatcac aggttaccta tacatctcag catggccaga cagcctgcct    1260
gaccttagcg tcctccagaa cctgcaagta atccggggac gaattctgca caatggcgcc    1320
tactcactga cctgcaagg gctgggcatc agctggctgg gctgcgctc gctgagggaa    1380
ctgggcagtg gactgccct catccaccat aacacccgcc tctgctttgt gcacacggtg    1440
ccctgggacc agctcttccg gaacccgcac caagccctgc tccacactgc caaccggcca    1500
gaggacgagt gtgtgggcga gggcctggcc tgccaccagc tgtgcgcccg agggcactgc    1560
tggggtccag ggcccaccca gtgtgtcaac tgcagccagt tccttcgggg ccaggagtgc    1620
gtggaggaat gccgagtact gcagggctc ccagggagt atgtgaatgc agacactgt    1680
ttgccgtgcc accctgagtg tcagcccag aatggctcag tgacatgttt tggaccggag    1740
gctgaccagt gtgtggcctg tgcccactat aaggaccctc ccttctgcgt ggcccgctgc    1800
cccagcggtg tgaaacctga cctctcctac atgcccatct ggaagtttcc agatgaggag    1860
ggcacgtgcc agtcttgccc catcaactgc acccactcct gtgtggacct ggatgacaag    1920
ggctgccccg ccgagcagag agccagccct ctgacgtcca tctctctgcc tgtggtgggc    1980
attctgctgg tcgtggtctt ggggtggtc tttggaatcc tcatcaagcg acggcagcag    2040
```

```
aagatccgga agtacacgat gcggaggctg ctgcaggaaa cggagctggt ggagccactg    2100
acaccgagtg gagcgatgcc caaccaggcg cagatgcgga tcctgaaaga cggagctg     2160 aggaaggtga aggtgcttgg atctggagct tttggcacag tctacaaggg catctggatc    2220
cctgatgggg agaatgtgaa aattccagtg gccatcaaag tgttgaggga aaacacatcc    2280
cccaaagcca acaaagaaat cttagacgaa gcatatgtga tggctggtgt gggctcccca    2340
tatgtctccc gcctcctggg catctgcctg acatccacgg tgcagctggt gacacagctt    2400
atgccctatg gctgcctctt agaccatgtc gagaaaacc gcggacgcct gggctcccag    2460
gacctgctga actggtgtat gcagattgcc aaggggatga gctacctgga ggatgtgcgg    2520
ctcgtacaca gggacttggc tgctcggaac gtgctggtca agagtcccaa ccatgtcaaa    2580
attacagact ttgggctggc tcggctgctg acattgacg agacagagta ccatgcagat    2640
gggggcaagg tgcccatcaa gtggatggcg ctggagtcca ttctccgacg gcggttcacc    2700
caccagagtg atgtgtggag ttatggtgtg actgtgtggg agctgatgac ttttggggcc    2760
aaaccttacg atgggatccc agcccggag atccctgacc tgctggaaaa ggggagcgg    2820 ctgccccagc cccccatctg caccattgat gtctacatga tcatggtcaa atgttggatg    2880
attgactctg aatgtcggcc gagattccgg gagttggtgt cggaattctc ccgcatggcc    2940
agggaccccc agcgctttgt ggtcatccag aatgaggact tgggcccagc cagtcccttg    3000
gacagcacct tctaccgctc actgctggag gacgatgaca tggggacct ggtggatgct    3060 gaggagtatc tggtaccca gcagggcttc ttctgtccag accctgcccc gggcactggg    3120
ggcatggtcc accacaggca ccgcagctca tctaccagga gtggcggtgg ggacctgacg    3180
ctagggctgg agccctctga gaggaggcc cccaggtctc cacgggcacc ctccgaaggg    3240
actggctctg atgtatttga tggtgaccta ggaatggggg cagccaaggg gctgcaaagc    3300
ctccccgcac atgaccccag ccctctacag cggtacagtg aggaccccac ggtacccctg    3360
ccttctgaga ctgacggcta cgttgccccc ctgacctgca gtccccagcc cgaatatgtg    3420
aaccagccag atgttcggcc acagccccct tcgccccaag agggccctct gtctcctgcc    3480
cgacctactg gtgccactct ggaaaggccc aagactctct ccccagggaa gaatggggtt    3540
gtcaaagacg ttttgccctt tggggtgct gtggagaacc ccgagtactt ggcacccgg    3600 ggaggagctg ccctcagcc ccaccttcct cctgccttca gcccagcctt cgacaacctc    3660
tattactggg accaggaccc atcagagcgg ggggctccac ctagcacctt caaagggaca    3720
cctacggcag agaacccaga gtacctgggt ctggacgtgc cagtgtga              3768
```

<210> SEQ ID NO 2
<211> LENGTH: 1255
<212> TYPE: PRT
<213> ORGANISM: Rhesus Monkey

<400> SEQUENCE: 2

```
Met Glu Leu Ala Ala Trp Tyr Arg Trp Gly Leu Leu Leu Ala Leu Leu
 1               5                  10                  15

Pro Pro Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60
```

-continued

```
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Leu Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Val Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Arg Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Leu Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr Arg Leu Cys Phe Val His Thr Val
465                 470                 475                 480

Pro Trp Asp Gln Leu Phe Arg Asn Pro His Gln Ala Leu Leu His Thr
```

-continued

```
                485                 490                 495
Ala Asn Arg Pro Glu Asp Glu Cys Val Gly Glu Gly Leu Ala Cys His
                500                 505                 510
Gln Leu Cys Ala Arg Gly His Cys Trp Gly Pro Gly Thr Gln Cys
                515                 520                 525
Val Asn Cys Ser Gln Phe Leu Arg Gly Gln Glu Cys Val Glu Cys
                530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
                595                 600                 605
Ser Tyr Met Pro Ile Trp Lys Phe Pro Asp Glu Glu Gly Thr Cys Gln
                610                 615                 620
Ser Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Leu Gly Val Val Phe Gly
                660                 665                 670
Ile Leu Ile Lys Arg Arg Gln Gln Lys Ile Arg Lys Tyr Thr Met Arg
                675                 680                 685
Arg Leu Leu Gln Glu Thr Glu Leu Val Glu Pro Leu Thr Pro Ser Gly
                690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
                755                 760                 765
Asp Glu Ala Tyr Val Met Ala Gly Val Gly Ser Pro Tyr Val Ser Arg
                770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
                820                 825                 830
Met Ser Tyr Leu Glu Asp Val Arg Leu Val His Arg Asp Leu Ala Ala
                835                 840                 845
Arg Asn Val Leu Val Lys Ser Pro Asn His Val Lys Ile Thr Asp Phe
850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
                900                 905                 910
```

```
Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr Leu
            1010                1015                1020

Val Pro Gln Gln Gly Phe Phe Cys Pro Asp Pro Ala Pro Gly Thr Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
                1060                1065                1070

Ser Pro Arg Ala Pro Ser Glu Gly Thr Gly Ser Asp Val Phe Asp Gly
            1075                1080                1085

Asp Leu Gly Met Gly Ala Ala Lys Gly Leu Gln Ser Leu Pro Ala His
            1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Gln Glu Gly Pro Leu Ser Pro Ala Arg Pro Thr Gly Ala Thr Leu Glu
            1155                1160                1165

Arg Pro Lys Thr Leu Ser Pro Gly Lys Asn Gly Val Val Lys Asp Val
            1170                1175                1180

Phe Ala Phe Gly Gly Ala Val Glu Asn Pro Glu Tyr Leu Ala Pro Arg
1185                1190                1195                1200

Gly Gly Ala Ala Pro Gln Pro His Leu Pro Ala Phe Ser Pro Ala
                1205                1210                1215

Phe Asp Asn Leu Tyr Tyr Trp Asp Gln Asp Pro Ser Glu Arg Gly Ala
                1220                1225                1230

Pro Pro Ser Thr Phe Lys Gly Thr Pro Thr Ala Glu Asn Pro Glu Tyr
            1235                1240                1245

Leu Gly Leu Asp Val Pro Val
            1250                1255

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
agccatgggg ccggagccgc a                                        21
```

```
<210> SEQ ID NO 4
<211> LENGTH: 26
<212> TYPE: DNA
<213> ORGANISM: Artificial Sequence
<220> FEATURE:
<223> OTHER INFORMATION: PCR Primer

<400> SEQUENCE: 4
agggctgggc agtgcagctc acagat                                          26

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
ctgcgggagc tgcagcttcg aag                                             23

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
ccaaagatct tcttgcagcc                                                 20

<210> SEQ ID NO 7
<211> LENGTH: 26
<212> TYPE: DNA
<213> ORGANISM: Artificial Sequence
<220> FEATURE:
<223> OTHER INFORMATION: PCR Primer

<400> SEQUENCE: 7
atctgtgagc tgcactgccc agccct                                          26

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gagcgcagcc ccagccagc                                                  19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
ggctgcaaga agatctttgg                                                 20

<210> SEQ ID NO 10
<211> LENGTH: 20
<212> TYPE: DNA
<213> ORGANISM: Artificial Sequence
<220> FEATURE:
<223> OTHER INFORMATION: PCR Primer
```

```
<400> SEQUENCE: 10
tgggtgcagt tgatggggca                                         20

<210> SEQ ID NO 11
<211> LENGTH: 44
<212> TYPE: DNA
<213> ORGANISM: Artificial Sequence
<220> FEATURE:
<223> OTHER INFORMATION: PCR Primer

<400> SEQUENCE: 11
ccagtttaaa catttaaatg ccgccaccat ggagctggcg gcct              44

<210> SEQ ID NO 12
<211> LENGTH: 26
<212> TYPE: DNA
<213> ORGANISM: Artificial Sequence
<220> FEATURE:
<223> OTHER INFORMATION: PCR Primer

<400> SEQUENCE: 12
tgctggggtc cagggcccac ccagtg                                  26

<210> SEQ ID NO 13
<211> LENGTH: 23
<212> TYPE: DNA
<213> ORGANISM: Artificial Sequence
<220> FEATURE:
<223> OTHER INFORMATION: PCR Primer

<400> SEQUENCE: 13
tcagggatct cccgggctgg gat                                     23

<210> SEQ ID NO 14
<211> LENGTH: 24
<212> TYPE: DNA
<213> ORGANISM: Artificial Sequence
<220> FEATURE:
<223> OTHER INFORMATION: PCR Primer

<400> SEQUENCE: 14
gtggaggaat gccgagtact gcag                                    24

<210> SEQ ID NO 15
<211> LENGTH: 39
<212> TYPE: DNA
<213> ORGANISM: Artificial Sequence
<220> FEATURE:
<223> OTHER INFORMATION: PCR Primer

<400> SEQUENCE: 15
tgtgttttcc ctcaacacgg cgatggccac tggaatttt                    39

<210> SEQ ID NO 16
<211> LENGTH: 39
<212> TYPE: DNA
<213> ORGANISM: Artificial Sequence
<220> FEATURE:
<223> OTHER INFORMATION: PCR Primer

<400> SEQUENCE: 16
aaaattccag tggccatcgc cgtgttgagg gaaaacaca                    39

<210> SEQ ID NO 17
```

```
<211> LENGTH: 23
<212> TYPE: DNA
<213> ORGANISM: Artificial Sequence
<220> FEATURE:
<223> OTHER INFORMATION: PCR Primer

<400> SEQUENCE: 17
ctgggcatct gcctgacatc cac                                              23

<210> SEQ ID NO 18
<211> LENGTH: 22
<212> TYPE: DNA
<213> ORGANISM: Artificial Sequence
<220> FEATURE:
<223> OTHER INFORMATION: PCR Primer

<400> SEQUENCE: 18
ggtttcaggg acagtctctg aa                                               22

<210> SEQ ID NO 19
<211> LENGTH: 32
<212> TYPE: DNA
<213> ORGANISM: Artificial Sequence
<220> FEATURE:
<223> OTHER INFORMATION: PCR Primer

<400> SEQUENCE: 19
gccgtcgact ttacatggca cgtccagacc ca                                    32

<210> SEQ ID NO 20
<211> LENGTH: 18
<212> TYPE: DNA
<213> ORGANISM: Artificial Sequence
<220> FEATURE:
<223> OTHER INFORMATION: PCR Primer

<400> SEQUENCE: 20
cttcatgtct gtgccggt                                                    18

<210> SEQ ID NO 21
<211> LENGTH: 22
<212> TYPE: DNA
<213> ORGANISM: Artificial Sequence
<220> FEATURE:
<223> OTHER INFORMATION: PCR Primer

<400> SEQUENCE: 21
ggccggagcc gcagtgagca cc                                               22

<210> SEQ ID NO 22
<211> LENGTH: 23
<212> TYPE: DNA
<213> ORGANISM: Artificial Sequence
<220> FEATURE:
<223> OTHER INFORMATION: PCR Primer

<400> SEQUENCE: 22
cttcgaagct gcagctcccg cag                                              23

<210> SEQ ID NO 23
<211> LENGTH: 25
<212> TYPE: DNA
<213> ORGANISM: Artificial Sequence
<220> FEATURE:
<223> OTHER INFORMATION: PCR Primer

<400> SEQUENCE: 23
```
atggagctgg cggccttgtg ccgct                           25

<210> SEQ ID NO 24
<211> LENGTH: 18
<212> TYPE: DNA
<213> ORGANISM: Artificial Sequence
<220> FEATURE:
<223> OTHER INFORMATION: PCR Primer

<400> SEQUENCE: 24
accggcacag acatgaag                                   18

<210> SEQ ID NO 25
<211> LENGTH: 26
<212> TYPE: DNA
<213> ORGANISM: Artificial Sequence
<220> FEATURE:
<223> OTHER INFORMATION: PCR Primer

<400> SEQUENCE: 25
cactgggtgg gccctggacc ccagca                          26

<210> SEQ ID NO 26
<211> LENGTH: 23
<212> TYPE: DNA
<213> ORGANISM: Artificial Sequence
<220> FEATURE:
<223> OTHER INFORMATION: PCR Primer

<400> SEQUENCE: 26
gatccaagca ccttcacctt cct                             23

<210> SEQ ID NO 27
<211> LENGTH: 19
<212> TYPE: DNA
<213> ORGANISM: Artificial Sequence
<220> FEATURE:
<223> OTHER INFORMATION: PCR Primer

<400> SEQUENCE: 27
gctggctggg gctgcgctc                                  19

<210> SEQ ID NO 28
<211> LENGTH: 23
<212> TYPE: DNA
<213> ORGANISM: Artificial Sequence
<220> FEATURE:
<223> OTHER INFORMATION: PCR Primer

<400> SEQUENCE: 28
gggatccaga tgcccttgta gac                             23

<210> SEQ ID NO 29
<211> LENGTH: 20
<212> TYPE: DNA
<213> ORGANISM: Artificial Sequence
<220> FEATURE:
<223> OTHER INFORMATION: PCR Primer

<400> SEQUENCE: 29
tgccccatca actgcaccca                                 20

<210> SEQ ID NO 30
<211> LENGTH: 23
<212> TYPE: DNA

<213> ORGANISM: Artificial Sequence
<220> FEATURE:
<223> OTHER INFORMATION: PCR Primer

<400> SEQUENCE: 30
gtggatgtca ggcagatgcc cag                                    23

<210> SEQ ID NO 31
<211> LENGTH: 23
<212> TYPE: DNA
<213> ORGANISM: Artificial Sequence
<220> FEATURE:
<223> OTHER INFORMATION: PCR Primer

<400> SEQUENCE: 31
aggaaggtga aggtgcttgg atc                                    23

<210> SEQ ID NO 32
<211> LENGTH: 26
<212> TYPE: DNA
<213> ORGANISM: Artificial Sequence
<220> FEATURE:
<223> OTHER INFORMATION: PCR Primer

<400> SEQUENCE: 32
taaggtttgg ccccaaaagt catcag                                 26

<210> SEQ ID NO 33
<211> LENGTH: 23
<212> TYPE: DNA
<213> ORGANISM: Artificial Sequence
<220> FEATURE:
<223> OTHER INFORMATION: PCR Primer

<400> SEQUENCE: 33
gtctacaagg gcatctggat ccc                                    23

<210> SEQ ID NO 34
<211> LENGTH: 23
<212> TYPE: DNA
<213> ORGANISM: Artificial Sequence
<220> FEATURE:
<223> OTHER INFORMATION: PCR Primer

<400> SEQUENCE: 34
ggctgggggc tgcaggtcag ggg                                    23

<210> SEQ ID NO 35
<211> LENGTH: 26
<212> TYPE: DNA
<213> ORGANISM: Artificial Sequence
<220> FEATURE:
<223> OTHER INFORMATION: PCR Primer

<400> SEQUENCE: 35
ctgatgactt ttggggccaa acctta                                 26

<210> SEQ ID NO 36
<211> LENGTH: 22
<212> TYPE: DNA
<213> ORGANISM: Artificial Sequence
<220> FEATURE:
<223> OTHER INFORMATION: PCR Primer

<400> SEQUENCE: 36
ttctgcggac ttggccttct gg                                     22

```
<210> SEQ ID NO 37
<211> LENGTH: 23
<212> TYPE: DNA
<213> ORGANISM: Artificial Sequence
<220> FEATURE:
<223> OTHER INFORMATION: PCR Primer

<400> SEQUENCE: 37
atcccagccc gggagatccc tga                                              23

<210> SEQ ID NO 38
<211> LENGTH: 17
<212> TYPE: DNA
<213> ORGANISM: Artificial Sequence
<220> FEATURE:
<223> OTHER INFORMATION: PCR Primer

<400> SEQUENCE: 38
tggcaggttc cctggga                                                     17

<210> SEQ ID NO 39
<211> LENGTH: 23
<212> TYPE: DNA
<213> ORGANISM: Artificial Sequence
<220> FEATURE:
<223> OTHER INFORMATION: PCR Primer

<400> SEQUENCE: 39
cccctgacct gcagcccca gcc                                               23

<210> SEQ ID NO 40
<211> LENGTH: 3768
<212> TYPE: DNA
<213> ORGANISM: Rhesus Monkey

<400> SEQUENCE: 40
atggagctgg cggcctggta ccgctggggg ctcctcctcg ccctcttgcc ccccggagct      60
gcgggcaccc aagtgtgcac cggcacagac atgaagctgc ggctccctgc cagtcccgag     120
acccacctgg acatgctccg ccacctctac cagggctgcc aggtggtgca gggtaacctg     180
gaactcacct acctgcccac caatgccagc ctctccttcc tgcaggatat ccaggaggtg     240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacccgctga acaataccac ccctgtcaca ggggcctccc aggaggcct gcgggagctg     420
cagcttcgaa gcctcacaga gatcttgaaa ggagggtct tgatccagcg gaaccccag     480
ctctgctacc aggacacgat tttgtggaag acatcttcc ataagaacaa ccagctggct     540
ctcacactga tcgacaccaa ccgctctcgg gcctgccacc cctgttctcc agtgtgtaag     600
ggctcccgct gctgggggaga gagttctgag gattgtcaga gcctgacgcg cactgtctgt     660
gccggtggct gtgcccgctg caaggggcca ctgcccactg actgctgcca tgagcagtgt     720
gctgccggct gcacgggccc caagcactct gactgcctgg cctgcctcca cttcaaccac     780
agcggcatct gtgarctgca ctgcccagcc ctggtcacct acaacacaga cacctttgag     840
tccatgccca accccgaggg ccggtataca ttcggcgcca gctgtgtgac tgcctgtccc     900
tacaactacc tttctacgga cgtgggatcc tgcaccctcg tctgcccct gcacaaccaa     960
gaggtgacag cggaggacgg aacacagcga tgtgagaagt gcagcaagcc ctgtgcccga    1020
```

```
gtgtgctatg gtctgggcat ggagcacttg cgagaggtga gggcggtcac cagtgccaat    1080
atccaggagt ttgctggctg caagaagatc tttgggagyt tggcatttct gccagagagc    1140
tttgatggcg acccagcctc caacaccgcc ccgcttcagc cggagcagct ccgagtgttt    1200
gagactctgg aagagatcac aggttaccta tacatctcag catggccaga cagcctgcct    1260
gaccttagcg tcctccagaa cctgcaagta atccggggac gaattctgca caatggcgcc    1320
tactcactga ccctgcaagg gctgggcatc agctggctgg ggctgcgctc gctgagggaa    1380
ctgggcagtg gactgcccct catccaccat aacacccgcc tctgctttgt gcacacggtg    1440
ccctgggacc agctcttccg gaacccgcac caagccctgc tccacactgc caaccggcca    1500
gaggacgagt gtgtgggcga gggcctggcc tgccaccagc tgtgcgcccr agggcactgc    1560
tggggtccag ggcccaccca gtgtgtcaac tgcagccagt tccttcgggg ccaggagtgc    1620
gtggaggaat gccgagtact gcagggctc ccagggagt atgtgaatgc agacactgt     1680
ttgccgtgcc accctgagtg tcagcccag aatggctcag tgacatgttt tggaccggag     1740
gctgaccagt gtgtggcctg tgcccactat aaggaccctc ccttctgcgt ggcccgctgc    1800
cccagcggtg tgaaacctga cctctcctac atgcccatct ggaagtttcc agatgaggag    1860
ggcacgtgcc agccttgccc catcaactgc acccactcct gtgtggacct ggatgacaag    1920
ggctgccccg ccgagcagar agccagccct ctgacgtcca tcatctctgc tgtggtgggc    1980
attctgctgg tcgtggtctt gggggtggtc tttggaatcc tcatcaagcg acggcagcag    2040
aagatccgga agtacacgat gcggaggctg ctgcaggaaa cggagctggt ggagccactg    2100
acaccgagtg gagcgatgcc caaccaggcg cagatgcgga tcctgaaaga acggagctg     2160
aggaaggtga aggtgcttgg atctggagct tttggcacag tctacaaggg catctggatc    2220
cctgatgggg agaatgtgaa aattccagtg gccatcaaag tgttgaggga aaacacatcc    2280
cccaaagcca caaagaaat cttagacgaa gcatatgtga tggctggtgt gggctcccca    2340
tatgtctccc gcctcctggg catctgcctg acatccacgg tgcagctggt gacacagctt    2400
atgcccatg ctgcctctt agaccatgtc cgagaaaacc gcggacgcct gggctcccag    2460
gacctgctga actggtgtat gcagattgcc aaggggatga gctacctgga ggatgtgcgg    2520
ctcgtacaca gggacttggc tgctcggaac gtgctggtca agagtcccaa ccatgtcaaa    2580
attacagact ttgggctggc tcggctgctg gacattgacg agacagagta ccatgcagat    2640
ggggcaagg tgcccatcaa gtggatggcg ctggagtcca ttctccgacg gcggttcacc    2700
caccagagtg atgtgtggag ttatggtgtg actgtgtggg agctgatgac ttttggggcc    2760
aaaccttacg atgggatccc agcccggag atccctgacc tgctggaaaa ggggagcgg    2820
ctgccccagc ccccatctg caccattgat gtctacatga tcatggtcaa atgttggatg    2880
attgactctg aatgtcggcc gagattccgg gagttggtgt cggaattctc ccgcatggcc    2940
agggaccccc agcgctttgt ggtcatccag aatgaggact gggcccagc cagtcccttg    3000
gacagcacct tctaccgctc actgctggag gacgatgaca tgggggacct ggtggatgct    3060
gaggagtatc tggtacccca gcagggcttc ttctgtccag accctgcccc gggcactggg    3120
ggcatggtcc accacaggca ccgcagctca tctaccagga gtggcggtgg ggacctgacg    3180
ctagggctgg agccctctga agaggaggcc cccaggtctc cacrggcacc ctccgaaggg    3240
actggctctg atgtatttga tggtgaccta ggaatggggg cagccaaggg gctgcaaagc    3300
ctccccgcac atgaccccag ccctctacag cggtacagtg aggaccccac ggtaccctg    3360
ccttctgaga ctgacggcta cgttgccccc ctgacctgca gyccccagcc cgaatatgtg    3420
```

-continued

```
aaccagccag atgttcggcc acagccccct tcgcccaag agggccctct gtctcctgcc    3480
cgacctactg gtgccactct ggaaaggccc aagactctct ccccagggaa gaatggggtt    3540
gtcaaagacg ttttgcctt tgggggtgct gtggagaacc ccgagtactt ggcaccccgg    3600
ggaggagctg cccctcagcc ccaccttcct cctgccttca gcccagcctt cgacaacctc    3660
tattactggg accaggaccc atcagagcgg ggggctccac ctagcacctt caaagggaca    3720
cctacggcag agaacccaga gtacctgggt ctggacgtgc cagtgtga                 3768
```

<210> SEQ ID NO 41
<211> LENGTH: 1255
<212> TYPE: PRT
<213> ORGANISM: Rhesus Monkey
<220> FEATURE:
<221> NAME/KEY: VARIANT
<222> LOCATION: 517, 647, 1075
<223> OTHER INFORMATION: Xaa = Any Amino Acid

<400> SEQUENCE: 41

```
Met Glu Leu Ala Ala Trp Tyr Arg Trp Gly Leu Leu Ala Leu Leu
 1               5                  10                  15

Pro Pro Gly Ala Ala Gly Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Val Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285
```

-continued

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Arg Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Leu Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
450                 455                 460

Leu Ala Leu Ile His His Asn Thr Arg Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Xaa Gly His Cys Trp Gly Pro Gly Pro Thr Gln Cys
            515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Thr Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Xaa Ala Ser Pro Leu Thr Ser Ile Ile Ser
            645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu

```
             705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
                755                 760                 765
Asp Glu Ala Tyr Val Met Ala Gly Val Gly Ser Pro Tyr Val Ser Arg
                770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
                820                 825                 830
Met Ser Tyr Leu Glu Asp Val Arg Leu Val His Arg Asp Leu Ala Ala
                835                 840                 845
Arg Asn Val Leu Val Lys Ser Pro Asn His Val Lys Ile Thr Asp Phe
850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
                900                 905                 910
Trp Glu Leu Met Thr Phe Gly Ala Lys Pro Tyr Asp Gly Ile Pro Ala
                915                 920                 925
Arg Glu Ile Pro Asp Leu Leu Glu Lys Gly Glu Arg Leu Pro Gln Pro
                930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
                980                 985                 990
Asp Leu Gly Pro Ala Ser Pro Leu Asp Ser Thr Phe Tyr Arg Ser Leu
                995                 1000                1005
Leu Glu Asp Asp Asp Met Gly Asp Leu Val Asp Ala Glu Glu Tyr Leu
                1010                1015                1020
Val Pro Gln Gln Gly Phe Phe Cys Pro Asp Pro Ala Pro Gly Thr Gly
1025                1030                1035                1040
Gly Met Val His His Arg His Arg Ser Ser Ser Thr Arg Ser Gly Gly
                1045                1050                1055
Gly Asp Leu Thr Leu Gly Leu Glu Pro Ser Glu Glu Ala Pro Arg
                1060                1065                1070
Ser Pro Xaa Ala Pro Ser Glu Gly Thr Gly Ser Asp Val Phe Asp Gly
                1075                1080                1085
Asp Leu Gly Met Gly Ala Ala Lys Gly Leu Gln Ser Leu Pro Ala His
                1090                1095                1100
Asp Pro Ser Pro Leu Gln Arg Tyr Ser Glu Asp Pro Thr Val Pro Leu
1105                1110                1115                1120
Pro Ser Glu Thr Asp Gly Tyr Val Ala Pro Leu Thr Cys Ser Pro Gln
                1125                1130                1135
```

Pro Glu Tyr Val Asn Gln Pro Asp Val Arg Pro Gln Pro Ser Pro
        1140                1145                1150

Gln Glu Gly Pro Leu Ser Pro Ala Arg Pro Thr Gly Ala Thr Leu Glu
        1155                1160                1165

Arg Pro Lys Thr Leu Ser Pro Gly Lys Asn Gly Val Val Lys Asp Val
        1170                1175                1180

Phe Ala Phe Gly Gly Ala Val Glu Asn Pro Glu Tyr Leu Ala Pro Arg
1185                1190                1195                1200

Gly Gly Ala Ala Pro Gln Pro His Leu Pro Ala Phe Ser Pro Ala
            1205                1210                1215

Phe Asp Asn Leu Tyr Tyr Trp Asp Gln Asp Pro Ser Glu Arg Gly Ala
            1220                1225                1230

Pro Pro Ser Thr Phe Lys Gly Thr Pro Thr Ala Glu Asn Pro Glu Tyr
            1235                1240                1245

Leu Gly Leu Asp Val Pro Val
        1250                1255

<210> SEQ ID NO 42
<211> LENGTH: 3768
<212> TYPE: DNA
<213> ORGANISM: Rhesus Monkey

<400> SEQUENCE: 42

```
atggagctgg cggcctggta ccgctggggg ctcctcctcg ccctcttgcc ccccggagct    60
gcgggcaccc aagtgtgcac cggcacagac atgaagctgc ggctccctgc cagtcccgag   120
acccacctgg acatgctccg ccacctctac cagggctgcc aggtggtgca gggtaacctg   180
gaactcacct acctgcccac caatgccagc ctctccttcc tgcaggatat ccaggaggtg   240
cagggctacg tgctcatcgc tcacaaccaa gtgaggcagg tcccactgca gaggctgcgg   300
attgtgcgag gcacccagct ctttgaggac aactatgccc tggccgtgct agacaatgga   360
gacctgctga acaataccac ccctgtcaca ggggcctccc aggaggcctg cgggagctg   420
cagcttcgaa gcctcacaga gatcttgaaa ggaggggtct tgatccagcg gaaccccag   480
ctctgctacc aggacacgat tttgtggaag acatcttcc ataagaacaa ccagctggct   540
ctcacactga tcgacaccaa ccgctctcgg gcctgccacc cctgttctcc agtgtgtaag   600
ggctcccgct gctggggaga gagttctgag gattgtcaga gcctgacgcg cactgtctgt   660
gccggtggct gtgcccgctg caaggggcca ctgcccactg actgctgcca tgagcagtgt   720
gctgccggct gcacgggccc caagcactct gactgcctgg cctgcctcca cttcaaccac   780
agcggcatct gtgaactgca ctgcccagcc ctggtcacct acaacacaga cacctttgag   840
tccatgccca accccgaggg ccggtataca ttcggcgcca gctgtgtgac tgcctgtccc   900
tacaactacc tttctacgga cgtgggatcc tgcaccctcg tctgccccct gcacaaccaa   960
gaggtgacag cggaggacgg aacacagcga tgtgagaagt gcagcaagcc ctgtgcccga  1020
gtgtgctatg gtctgggcat ggagcacttg cgagaggtga gggcggtcac cagtgccaat  1080
atccaggagt ttgctggctg caagaagatc tttgggagct ggcatttct gccagagagc  1140
tttgatggcg acccagcctc caacaccgcc ccgcttcagc cggagcagct ccgagtgttt  1200
gagactctgg aagagatcac aggttaccta tacatctcag catggccaga cagcctgcct  1260
gaccttagcg tcctccagaa cctgcaagta atccggggac gaattctgca caatggcgcc  1320
tactcactga ccctgcaagg gctgggcatc agctggctgg gctgcgctc gctgagggaa  1380
```

```
ctgggcagtg gactggccct catccaccat aacacccgcc tctgctttgt gcacacggtg   1440
ccctgggacc agctcttccg gaacccgcac caagccctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccaggagt atgtgaatgc cagacactgt   1680
ttgccgtgcc accctgagtg tcagcccag aatggctcag tgacatgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcacgtgcc agtcttgccc catcaactgc acccactcct gtgtggacct ggatgacaag   1920
ggctgccccg ccgagcagag agccagccct ctgacgtcca tcatctctgc tgtggtgggc   1980
attctgctgg tcgtggtctt gggggtggtc tttggaatcc tcatcaagcg acggcagcag   2040
aagatccgga gtacacgat gcggaggctg ctgcaggaaa cggagctggt ggagccactg   2100
acaccgagtg gagcgatgcc caaccaggcg cagatgcgga tcctgaaaga cggagctgg   2160 aggaaggtga aggtgcttgg atctggagct tttggcacag tctacaaggg catctggatc   2220
cctgatgggg agaatgtgaa aattccagtg gccatcaaag tgttgaggga aaacacatcc   2280
cccaaagcca caaagaaat cttagacgaa gcatatgtga tggctggtgt gggctcccca   2340
tatgtctccc gcctcctggg catctgcctg acatccacgg tgcagctggt gacacagctt   2400 atgcccctatg gctgcctctt agaccatgtc cgagaaaacc gcggacgcct gggctcccag   2460
gacctgctga actggtgtat gcagattgcc aaggggatga gctacctgga ggatgtgcgg   2520
ctcgtacaca gggacttggc tgctcggaac gtgctggtca agagtcccaa ccatgtcaaa   2580
attacagact ttgggctggc tcggctgctg gacattgacg agacagagta ccatgcagat   2640
gggggcaagg tgcccatcaa gtggatggcg ctggagtcca ttctccgacg gcggttcacc   2700
caccagagtg atgtgtggag ttatggtgtg actgtgtggg agctgatgac ttttggggcc   2760
aaaccttacg atgggatccc agcccgggag atccctgacc tgctggaaaa ggggagcgg   2820 ctgccccagc cccccatctg caccattgat gtctacatga tcatggtcaa atgttggatg   2880
attgactctg aatgtcggcc gagattccgg gagttggtgt cggaattctc ccgcatggcc   2940
agggaccccc agcgctttgt ggtcatccag aatgaggact gggcccagc cagtcccttg   3000 gacagcacct tctaccgctc actgctggag gacgatgaca tggggacct ggtggatgct   3060 gaggagtatc tggtacccca gcagggcttc ttctgtccag accctgcccc gggcactggg   3120
ggcatggtcc accacaggca ccgcagctca tctaccagga gtggcggtgg ggacctgacg   3180
ctagggctgg agccctctga agaggaggcc cccagtctc cacgggcacc ctccgaaggg   3240
actggctctg atgtatttga tggtgaccta ggaatggggg cagccaaggg gctgcaaagc   3300
ctccccgcac atgacccag ccctctacag cggtacagtg aggacccac ggtacccctg   3360 ccttctgaga ctgacggcta cgttgccccc ctgacctgca gtcccagcc cgaatatgtg   3420 aaccagccaa atgttcggcc acagcccct tcgccccaag agggccctct gtctcctgcc   3480
cgacctactg gtgccactct ggaaaggccc aagactctct ccccagggaa gaatggggtt   3540
gtcaaagacg tttttgcctt tgggggtgct gtggagaacc ccgagtactt ggcaccccgg   3600
ggaggagctg ccctcagcc ccacttcct cctgccttca gcccagcctt cgacaacctc   3660
tattactggg accaggaccc catcagagcgg ggggctccac ctagcacctt caaagggaca   3720
cctacggcag agaacccaga gtacctgggt ctggacgtgc agtgtga             3768
```

<210> SEQ ID NO 43
<211> LENGTH: 3768
<212> TYPE: DNA
<213> ORGANISM: Rhesus Monkey

<400> SEQUENCE: 43

| | | | | | |
|---|---|---|---|---|---|
| atggagctgg | cggcctggta | ccgctggggg | ctcctcctcg | ccctcttgcc | ccccggagct | 60 |
| gcgggcaccc | aagtgtgcac | cggcacagac | atgaagctgc | ggctccctgc | cagtcccgag | 120 |
| acccacctgg | acatgctccg | ccacctctac | cagggctgcc | aggtggtgca | gggtaacctg | 180 |
| gaactcacct | acctgcccac | caatgccagc | ctctccttcc | tgcaggatat | ccaggaggtg | 240 |
| cagggctacg | tgctcatcgc | tcacaaccaa | gtgaggcagg | tcccactgca | gaggctgcgg | 300 |
| attgtgcgag | gcacccagct | ctttgaggac | aactatgccc | tggccgtgct | agacaatgga | 360 |
| gacctgctga | caataccac | ccctgtcaca | ggggcctccc | caggaggcct | gcgggagctg | 420 |
| cagcttcgaa | gcctcacaga | gatcttgaaa | ggaggggtct | tgatccagcg | gaaccccag | 480 |
| ctctgctacc | aggacacgat | tttgtggaag | gacatcttcc | ataagaacaa | ccagctggct | 540 |
| ctcacactga | tcgacaccaa | ccgctctcgg | gcctgccacc | cctgttctcc | agtgtgtaag | 600 |
| ggctcccgct | gctggggaga | gagttctgag | gattgtcaga | gcctgacgcg | cactgtctgt | 660 |
| gccggtggct | gtgcccgctg | caaggggcca | ctgcccactg | actgctgcca | tgagcagtgt | 720 |
| gctgccggct | gcacgggccc | caagcactct | gactgcctgg | cctgcctcca | cttcaaccac | 780 |
| agcggcatct | gtgagctgca | ctgcccagcc | ctggtcacct | acaacacaga | cacctttgag | 840 |
| tccatgccca | accccgaggg | ccggtataca | ttcggcgcca | gctgtgtgac | tgcctgtccc | 900 |
| tacaactacc | tttctacgga | cgtgggatcc | tgcaccctcg | tctgccccct | gcacaaccaa | 960 |
| gaggtgacag | cggaggacgg | aacacagcga | tgtgagaagt | gcagcaagcc | ctgtgcccga | 1020 |
| gtgtgctatg | gtctgggcat | ggagcacttg | cgagaggtga | gggcggtcac | cagtgccaat | 1080 |
| atccaggagt | ttgctggctg | caagaagatc | tttgggagct | tggcatttct | gccagagagc | 1140 |
| tttgatggcg | acccagcctc | caacaccgcc | ccgcttcagc | cggagcagct | ccgagtgttt | 1200 |
| gagactctgg | aagagatcac | aggttaccta | tacatctcag | catggccaga | cagcctgcct | 1260 |
| gaccttagcg | tcctccagaa | cctgcaagta | atccggggac | gaattctgca | caatggcgcc | 1320 |
| tactcactga | ccctgcaagg | gctgggcatc | agctggctgg | ggctgcgctc | gctgagggaa | 1380 |
| ctgggcagtg | gactggccct | catccaccat | aacacccgcc | tctgctttgt | gcacacggtg | 1440 |
| ccctgggacc | agctcttccg | gaacccgcac | caagccctgc | tccacactgc | caaccggcca | 1500 |
| gaggacgagt | gtgtgggcga | gggcctggcc | tgccaccagc | tgtgcgcccg | agggcactgc | 1560 |
| tggggtccag | ggcccaccca | gtgtgtcaac | tgcagccagt | ccttcggg | ccaggagtgc | 1620 |
| gtggaggaat | gccgagtact | gcaggggctc | ccagggagt | atgtgaatgc | cagacactgt | 1680 |
| ttgccgtgcc | accctgagtg | tcagccccag | aatggctcag | tgacatgttt | tggaccggag | 1740 |
| gctgaccagt | gtgtggcctg | tgcccactat | aaggaccctc | ccttctgcgt | ggcccgctgc | 1800 |
| cccagcggtg | tgaaacctga | cctctcctac | atgcccatct | ggaagtttcc | agatgaggag | 1860 |
| ggcacgtgcc | agtcttgccc | catcaactgc | acccactcct | gtgtggacct | ggatgacaag | 1920 |
| ggctgccccg | ccgagcagag | agccagccct | ctgacgtcca | tcatctctgc | tgtggtgggc | 1980 |
| attctgctgg | tcgtggtctt | ggggtggc | tttggaatcc | tcatcaagcg | acggcagcag | 2040 |
| aagatccgga | agtacacgat | gcggaggctg | ctgcaggaaa | cggagctggt | ggagccactg | 2100 |

-continued

```
acaccgagtg gagcgatgcc caaccaggcg cagatgcgga tcctgaaaga gacggagctg    2160
aggaaggtga aggtgcttgg atctggagct tttggcacag tctacaaggg catctggatc    2220
cctgatgggg agaatgtgaa aattccagtg gccatcaaag tgttgaggga aaacacatcc    2280
cccaaagcca acaaagaaat cttagacgaa gcatatgtga tggctggtgt gggctcccca    2340
tatgtctccc gcctcctggg catctgcctg acatccacgg tgcagctggt gacacagctt    2400
atgccctatg gctgcctctt agaccatgtc cgagaaaacc gcggacgcct gggctcccag    2460
gacctgctga actggtgtat gcagattgcc aagggatga gctacctgga ggatgtgcgg    2520
ctcgtacaca gggacttggc tgctcggaac gtgctggtca agagtccaa ccatgtcaaa    2580
attacagact ttgggctggc tcggctgctg gacattgacg agacagagta ccatgcagat    2640
gggggcaagg tgcccatcaa gtggatgcg ctggagtcca ttctccgacg gcggttcacc    2700
caccagagtg atgtgtggag ttatggtgtg actgtgtggg agctgatgac ttttggggcc    2760
aaaccttacg atgggatccc agcccggag atccctgacc tgctggaaaa gggggagcgg    2820
ctgccccagc cccccatctg caccattgat gtctacatga tcatggtcaa atgttggatg    2880
attgactctg aatgtcggcc gagattccgg gagttggtgt cggaattctc ccgcatggcc    2940
agggacccc agcgctttgt ggtcatccag aatgaggact tgggcccagc cagtcccttg    3000
gacagcacct tctaccgctc actgctggag gacgatgaca tggggggacct ggtggatgct    3060
gaggagtatc tggtaccca gcagggcttc ttctgtccag accctgcccc gggcactggg    3120
ggcatggtcc accacaggca ccgcagctca tctaccagga gtggcggtgg ggacctgacg    3180
ctagggctgg agccctctga agaggaggcc cccaggtctc cacgggcacc ctccgaaggg    3240
actggctctg atgtatttga tggtgaccta ggaatggggg cagccaaggg gctgcaaagc    3300
ctccccgcac atgacccag ccctctacag cggtacagtg aggacccccac ggtacccctg    3360
ccttctgaga ctgacggcta cgttgccccc ctgacctgca gtccccagcc cgaatatgtg    3420
aaccagccag atgttcggcc acagcccct tcgccccaag agggccctct gtctcctgcc    3480
cgacctactg gtgccactct ggaaaggccc aagactctct ccccagggaa gaatgggggtt    3540
gtcaaagacg tttttgcctt tggggggtgct gtggagaacc ccgagtactt ggcaccccgg    3600
ggaggagctg cccctcagcc ccaccttcct cctgccttca gcccagcctt cgacaacctc    3660
tattactggg accaggaccc atcagagcgg ggggctccac ctagcaccctt caaagggaca    3720
cctacggcag agaacccaga gtacctgggt ctggacgtgc cagtgtga              3768
```